US012211626B2

United States Patent
Jancsary et al.

(10) Patent No.: US 12,211,626 B2
(45) Date of Patent: *Jan. 28, 2025

(54) MEDICAL INTELLIGENCE SYSTEM AND METHOD

(71) Applicant: Microsoft Technology Licensing, LLC, Redmond, WA (US)

(72) Inventors: Jeremy Martin Jancsary, Vienna (AT); Joel Praveen Pinto, Aachen (DE); Uwe Helmut Jost, Groton, MA (US); William F. Ganong, III, Brookline, MA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/666,854

(22) Filed: Feb. 8, 2022

(65) Prior Publication Data
US 2022/0254517 A1 Aug. 11, 2022

Related U.S. Application Data

(60) Provisional application No. 63/148,458, filed on Feb. 11, 2021.

(51) Int. Cl.
*G16H 80/00* (2018.01)
*G16H 10/20* (2018.01)
(Continued)

(52) U.S. Cl.
CPC ............ *G16H 80/00* (2018.01); *G16H 10/60* (2018.01); *G16H 20/10* (2018.01); *G16H 30/40* (2018.01);
(Continued)

(58) Field of Classification Search
CPC .................................................... G16H 80/00
See application file for complete search history.

(56) References Cited

U.S. PATENT DOCUMENTS 8,548,828 B1 10/2013 Longmire
10,628,553 B1 4/2020 Murrish
(Continued)

FOREIGN PATENT DOCUMENTS

CN 110024026 A 7/2019
EP 3719809 A1 10/2020
(Continued)

OTHER PUBLICATIONS

"International Search Report and Written Opinion Issued in PCT Application No. PCT/US22/015642", Mailed Date: Jun. 2, 2022, 9 Pages.
(Continued)

*Primary Examiner* — Joseph H Feild
*Assistant Examiner* — Pameshanand Mahase
(74) *Attorney, Agent, or Firm* — Brian J. Colandreo; Heath M. Sargeant; Holland & Knight LLP

(57) ABSTRACT

A method, computer program product, and computing system for: monitoring a meeting between a patient and a medical entity during a medical encounter; gathering information during the medical encounter, thus generating gathered encounter information; generating medical encounter topical information via artificial intelligence, wherein the medical encounter topical information is based at least in part upon the gathered encounter information and is configured to provide guidance to the medical entity concerning one or more topics to be discussed during the medical encounter; and providing the medical encounter topical information to the medical entity.

27 Claims, 18 Drawing Sheets

(51) Int. Cl.
| | |
|---|---|
| *G16H 10/60* | (2018.01) |
| *G16H 20/10* | (2018.01) |
| *G16H 30/40* | (2018.01) |
| *G16H 40/20* | (2018.01) |
| *G16H 40/63* | (2018.01) |
| *G16H 40/67* | (2018.01) |
| *G16H 50/20* | (2018.01) |

(52) U.S. Cl.
CPC ............. *G16H 40/20* (2018.01); *G16H 40/63* (2018.01); *G16H 40/67* (2018.01); *G16H 50/20* (2018.01)

(56) References Cited

U.S. PATENT DOCUMENTS

| | | |
|---|---|---|
| 11,488,712 B2 | 11/2022 | Lee |
| 11,515,021 B2 | 11/2022 | Mason |
| 11,742,092 B2 | 8/2023 | Murrish |
| 2002/0115912 A1 | 8/2002 | Muraki |
| 2003/0110059 A1 | 6/2003 | John, III |
| 2003/0181790 A1 | 9/2003 | David |
| 2005/0055246 A1 | 3/2005 | Simon |
| 2005/0149364 A1 | 7/2005 | Ombrellaro |
| 2005/0273363 A1 | 12/2005 | Lipscher et al. |
| 2007/0127795 A1 | 6/2007 | Lau et al. |
| 2007/0234219 A1 | 10/2007 | Bhattaru |
| 2008/0242977 A1 | 10/2008 | Sirohey et al. |
| 2009/0138285 A1 | 5/2009 | Denberg |
| 2009/0259492 A1 | 10/2009 | Cossman |
| 2010/0109860 A1 | 5/2010 | Williamson et al. |
| 2011/0166465 A1 | 7/2011 | Clements et al. |
| 2011/0246225 A1 | 10/2011 | Green et al. |
| 2012/0173281 A1 | 7/2012 | Dilella et al. |
| 2015/0154355 A1 | 6/2015 | Lin |
| 2015/0213224 A1* | 7/2015 | Amarasingham ...... G16H 50/30 705/2 |
| 2016/0071547 A1 | 3/2016 | Sugawara |
| 2016/0110504 A1 | 4/2016 | Fialkov |
| 2016/0128647 A1 | 5/2016 | King |
| 2016/0140318 A1 | 5/2016 | Stangel |
| 2016/0148375 A1 | 5/2016 | Oh et al. |
| 2016/0180743 A1 | 6/2016 | Ahmad |
| 2016/0188843 A1 | 6/2016 | Staples, II |
| 2016/0302666 A1 | 10/2016 | Shaya |
| 2017/0116384 A1 | 4/2017 | Ghani |
| 2017/0235905 A1 | 8/2017 | Santiago, Jr. |
| 2017/0329922 A1 | 11/2017 | Eberting |
| 2018/0121606 A1* | 5/2018 | Allen ..................... G16H 10/60 |
| 2018/0121728 A1 | 5/2018 | Wells |
| 2018/0181712 A1 | 6/2018 | Ensey et al. |
| 2018/0211730 A1* | 7/2018 | Slepian .................. G16H 10/60 |
| 2018/0226158 A1 | 8/2018 | Fish et al. |
| 2018/0247024 A1 | 8/2018 | Divine et al. |
| 2018/0261307 A1 | 9/2018 | Couse et al. |
| 2018/0316947 A1 | 11/2018 | Todd |
| 2018/0330059 A1 | 11/2018 | Bates et al. |
| 2018/0356244 A1 | 12/2018 | Han et al. |
| 2019/0065970 A1 | 2/2019 | Bonutti |
| 2019/0156921 A1 | 5/2019 | Kohli |
| 2019/0189259 A1 | 6/2019 | Clark |
| 2019/0272147 A1 | 9/2019 | Vozila et al. |
| 2019/0272901 A1 | 9/2019 | Almendro Barreda et al. |
| 2020/0004561 A1 | 1/2020 | Kottler |
| 2020/0066414 A1* | 2/2020 | Neff .................... H04L 12/1818 |
| 2020/0221951 A1 | 7/2020 | Amble |
| 2020/0228616 A1 | 7/2020 | Nishikawa |
| 2020/0258510 A1 | 8/2020 | Lavery et al. |
| 2020/0279659 A1 | 9/2020 | De Brouwer et al. |
| 2020/0398063 A1 | 12/2020 | Debates et al. |
| 2020/0402656 A1 | 12/2020 | Debates |
| 2021/0082554 A1* | 3/2021 | Kalia ........................ G06N 3/08 |
| 2021/0118555 A1 | 4/2021 | Dreyer |
| 2021/0142903 A1 | 5/2021 | Mason |
| 2021/0182932 A1 | 6/2021 | Bello, Jr. |
| 2021/0295963 A1 | 9/2021 | Bakshi |
| 2021/0335503 A1 | 10/2021 | Williams, III |
| 2021/0375489 A1 | 12/2021 | Tsushita |
| 2022/0254480 A1 | 8/2022 | Jancsary et al. |
| 2022/0254485 A1 | 8/2022 | Jancsary et al. |
| 2022/0254495 A1 | 8/2022 | Jancsary et al. |
| 2022/0254496 A1 | 8/2022 | Jancsary et al. |
| 2022/0254514 A1 | 8/2022 | Jancsary et al. |
| 2022/0254515 A1 | 8/2022 | Jancsary et al. |
| 2022/0254516 A1 | 8/2022 | Jancsary et al. |

FOREIGN PATENT DOCUMENTS

| | | |
|---|---|---|
| JP | 2019101715 A | 6/2019 |
| WO | 2014205079 A2 | 12/2014 |

OTHER PUBLICATIONS

"International Search Report and Written Opinion Issued in PCT Application No. PCT/US22/015649", Mailed Date: Apr. 19, 2022, 7 Pages.

"International Search Report and Written Opinion Issued in PCT Application No. PCT/US22/015651", Mailed Date: Apr. 28, 2022, 7 Pages.

"International Search Report and Written Opinion Issued in PCT Application No. PCT/US22/015654", Mailed Date: Jun. 1, 2022, 7 Pages.

"International Search Report and Written Opinion Issued in PCT Application No. PCT/US22/015657", Mailed Date: May 3, 2022, 8 Pages.

"International Search Report and Written Opinion Issued in PCT Application No. PCT/US22/015660", Mailed Date: May 23, 2022, 9 Pages.

"International Search Report and Written Opinion Issued in PCT Application No. PCT/US22/015667", Mailed Date: May 24, 2022, 7 Pages.

"International Search Report and Written Opinion Issued in PCT Application No. PCT/US22/015671", Mailed Date: May 23, 2022, 9 Pages.

"Non Final Office Action Issued in U.S. Appl. No. 17/666,780", Mailed Date: Oct. 4, 2023, 23 Pages.

"Non Final Office Action Issued in U.S. Appl. No. 17/666,828", Mailed Date: Sep. 13, 2023, 19 Pages.

"Non Final Office Action Issued in U.S. Appl. No. 17/666,847", Mailed Date: Sep. 27, 2023, 41 Pages.

Final Office Action mailed on Feb. 28, 2024, in U.S. Appl. No. 17/666,828, 18 pages.

Final Office Action mailed on Jan. 19, 2024, in U.S. Appl. No. 17/666,780, 24 pages.

U.S. Appl. No. 17/666,780, filed Feb. 8, 2022.
U.S. Appl. No. 17/666,828, filed Feb. 8, 2022.
U.S. Appl. No. 17/666,817, filed Feb. 8, 2022.
U.S. Appl. No. 17/666,787, filed Feb. 8, 2022.
U.S. Appl. No. 17/666,798, filed Feb. 8, 2022.
U.S. Appl. No. 17/666,839, filed Feb. 8, 2022.
U.S. Appl. No. 17/666,847, filed Feb. 8, 2022.

Final Office Action mailed on Jan. 12, 2024, in U.S. Appl. No. 17/666,847, 46 pages.

Non-Final Office Action mailed on Dec. 20, 2023, in U.S. Appl. No. 17/666,839, 15 pages.

Non-Final Office Action mailed on Mar. 22, 2024, in U.S. Appl. No. 17/666,847, 55 pages.

Non-Final Office Action mailed on Mar. 27, 2024, in U.S. Appl. No. 17/666,780, 27 pages.

Non-Final Office Action mailed on Jun. 4, 2024, in U.S. Appl. No. 17/666,817, 15 pages.

Non-Final Office Action mailed on Jun. 6, 2024, in U.S. Appl. No. 17/666,787, 13 pages.

Final Office Action mailed on Aug. 12, 2024, in U.S. Appl. No. 17/666,847, 58 pages.

Final Office Action mailed on Aug. 19, 2024, in U.S. Appl. No. 17/666,839, 17 pages.

(56) References Cited

OTHER PUBLICATIONS

Final Office Action mailed on Jul. 18, 2024, in U.S. Appl. No. 17/666,780, 28 pages.
Non-Final Office Action issued in U.S. Appl. No. 17/666,828, mailed on Jun. 20, 2024, 26 Pages.
Final Office Action mailed on Oct. 1, 2024, in U.S. Appl. No. 17/666,787, 17 pages.
Notice of Allowance mailed on Oct. 9, 2024, in U.S. Appl. No. 17/666,828, 09 pages.
Notice of Allowance mailed on Sep. 30, 2024, in U.S. Appl. No. 17/666,780, 10 pages.
Extended European Search Report Received for European Application No. 22753207.4, mailed on Nov. 22, 2024, 10 pages.

* cited by examiner

MEDICAL INTELLIGENCE SYSTEM AND METHOD

RELATED APPLICATION(S)

This application claims the benefit of U.S. Provisional Application No. 63/148,458, filed on 11 Feb. 2021, the entire contents of which is herein incorporated by reference.

TECHNICAL FIELD

This disclosure relates to intelligence systems and methods and, more particularly, to intelligence systems and methods within the medical space.

BACKGROUND

As is known in the art, cooperative intelligence is the creation of reports and documentation that details the history of an event/individual. As would be expected, traditional documentation includes various types of data, examples of which may include but are not limited to paper-based documents and transcripts, as well as various images and diagrams. As the healthcare world moved from paper-based content to digital content, traditional medical documentation also moved in that direction, where medical reports and documentation were gradually transitioned from stacks of paper geographically-dispersed across multiple locations/institutions to consolidated and readily accessible digital content.

As is known, regular access to medical professionals is of paramount importance for people maintaining their health. Accordingly, it has been shown that annual physicals are instrumental to maintaining a patient's health. Further and in the event of an illness, it is important that a medical professional is engaged in a timely fashion. Unfortunately, such medical professionals are often not timely engaged. For example, it is often difficult for people to travel to see a doctor. Further and especially when a specialist is needed, a significant amount of travel may be required in order to visit with such a medical professional. Accordingly, telehealth visits may solve some of these issues by allowing a patient to visit with a doctor without having to actually travel to the doctor's office.

SUMMARY OF DISCLOSURE

Concept 8

In one implementation, a computer-implemented method is executed on a computing system and includes: monitoring a meeting between a patient and a medical entity during a medical encounter; gathering information during the medical encounter, thus generating gathered encounter information; generating medical encounter topical information via artificial intelligence, wherein the medical encounter topical information is based at least in part upon the gathered encounter information and is configured to provide guidance to the medical entity concerning one or more topics to be discussed during the medical encounter; and providing the medical encounter topical information to the medical entity.

One or more of the following features may be included. The medical entity may include one or more of: a medical professional; and a medical virtual assistant. The meeting may include one or more of: an intake portion; a consultation portion; and a follow-up portion. The medical encounter may include one or more of: an in-person medical encounter; and a telehealth medical encounter. Providing the medical encounter topical information to the medical entity may include: providing the medical encounter topical information to the medical entity via an informational window. The informational window may be a transparent overlay informational window. Generating medical encounter topical information via artificial intelligence may include: generating initial medical encounter topical information in response to initial information gathered during the medical encounter; and generating supplemental medical encounter topical information in response to supplemental information gathered during the medical encounter. The medical encounter topical information may be based upon one or more best practices. The one or more best practices may be definable by one or more medical organizations/institutions. Feedback concerning the medical encounter topical information may be received from the medical entity.

In another implementation, a computer program product resides on a computer readable medium and has a plurality of instructions stored on it. When executed by a processor, the instructions cause the processor to perform operations including: monitoring a meeting between a patient and a medical entity during a medical encounter; gathering information during the medical encounter, thus generating gathered encounter information; generating medical encounter topical information via artificial intelligence, wherein the medical encounter topical information is based at least in part upon the gathered encounter information and is configured to provide guidance to the medical entity concerning one or more topics to be discussed during the medical encounter; and providing the medical encounter topical information to the medical entity.

One or more of the following features may be included. The medical entity may include one or more of: a medical professional; and a medical virtual assistant. The meeting may include one or more of: an intake portion; a consultation portion; and a follow-up portion. The medical encounter may include one or more of: an in-person medical encounter; and a telehealth medical encounter. Providing the medical encounter topical information to the medical entity may include: providing the medical encounter topical information to the medical entity via an informational window. The informational window may be a transparent overlay informational window. Generating medical encounter topical information via artificial intelligence may include: generating initial medical encounter topical information in response to initial information gathered during the medical encounter; and generating supplemental medical encounter topical information in response to supplemental information gathered during the medical encounter. The medical encounter topical information may be based upon one or more best practices. The one or more best practices may be definable by one or more medical organizations/institutions. Feedback concerning the medical encounter topical information may be received from the medical entity.

In another implementation, a computing system includes a processor and memory is configured to perform operations including: monitoring a meeting between a patient and a medical entity during a medical encounter; gathering information during the medical encounter, thus generating gathered encounter information; generating medical encounter topical information via artificial intelligence, wherein the medical encounter topical information is based at least in part upon the gathered encounter information and is configured to provide guidance to the medical entity concerning one or more topics to be discussed during the medical encounter; and providing the medical encounter topical information to the medical entity.

One or more of the following features may be included. The medical entity may include one or more of: a medical professional; and a medical virtual assistant. The meeting may include one or more of: an intake portion; a consultation portion; and a follow-up portion. The medical encounter may include one or more of: an in-person medical encounter; and a telehealth medical encounter. Providing the medical encounter topical information to the medical entity may include: providing the medical encounter topical information to the medical entity via an informational window. The informational window may be a transparent overlay informational window. Generating medical encounter topical information via artificial intelligence may include: generating initial medical encounter topical information in response to initial information gathered during the medical encounter; and generating supplemental medical encounter topical information in response to supplemental information gathered during the medical encounter. The medical encounter topical information may be based upon one or more best practices. The one or more best practices may be definable by one or more medical organizations/institutions. Feedback concerning the medical encounter topical information may be received from the medical entity.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Ambient Cooperative Intelligence (In-Person Encounters) System Overview

Figure 1:
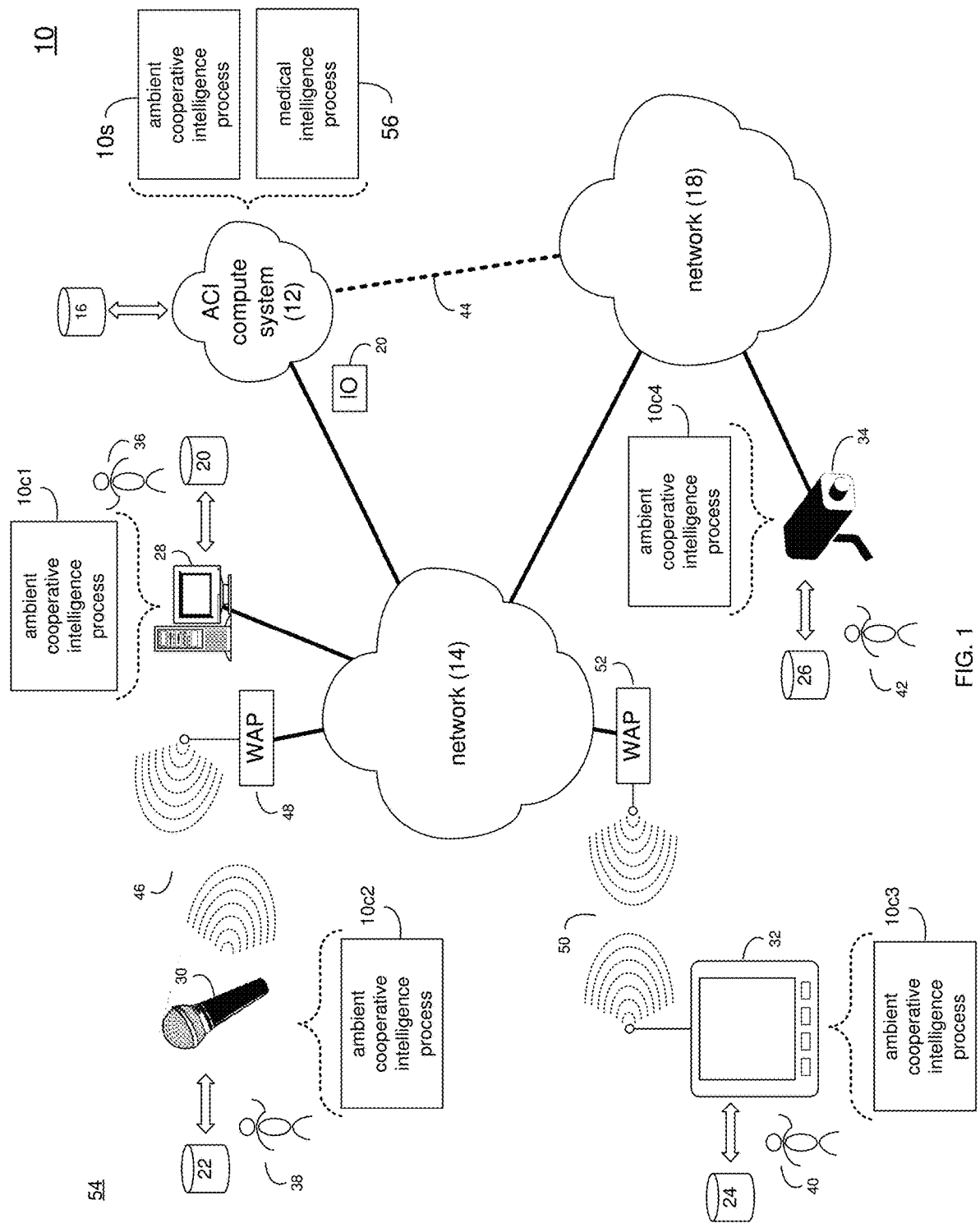
FIG. 1 is a diagrammatic view of an ambient cooperative intelligence compute system, an ambient cooperative intelligence process and a medical intelligence process coupled to a distributed computing network.

Referring to FIG. 1, there is shown ambient cooperative intelligence process 10. As will be discussed below in greater detail, ambient cooperative intelligence process 10 may be configured to automate the collection and processing of encounter information to generate/store/distribute reports.

Ambient cooperative intelligence process 10 may be implemented as a server-side process, a client-side process, or a hybrid server-side/client-side process. For example, ambient cooperative intelligence process 10 may be implemented as a purely server-side process via ambient cooperative intelligence process 10s. Alternatively, ambient cooperative intelligence process 10 may be implemented as a purely client-side process via one or more of ambient cooperative intelligence process 10c1, ambient cooperative intelligence process 10c2, ambient cooperative intelligence process 10c3, and ambient cooperative intelligence process 10c4. Alternatively still, ambient cooperative intelligence process 10 may be implemented as a hybrid server-side/client-side process via ambient cooperative intelligence process 10s in combination with one or more of ambient cooperative intelligence process 10c1, ambient cooperative intelligence process 10c2, ambient cooperative intelligence process 10c3, and ambient cooperative intelligence process 10c4.

Accordingly, ambient cooperative intelligence process 10 as used in this disclosure may include any combination of ambient cooperative intelligence process 10s, ambient cooperative intelligence process 10c1, ambient cooperative intelligence process 10c2, ambient cooperative intelligence process 10c3, and ambient cooperative intelligence process 10c4.

Ambient cooperative intelligence process 10s may be a server application and may reside on and may be executed by ambient cooperative intelligence (ACI) compute system 12, which may be connected to network 14 (e.g., the Internet or a local area network). ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACI compute system 12 may execute one or more operating systems, examples of which may include but are not limited to: Microsoft Windows Server™; Redhat Linux™, Unix, or a custom operating system, for example.

The instruction sets and subroutines of ambient cooperative intelligence process 10s, which may be stored on storage device 16 coupled to ACI compute system 12, may be executed by one or more processors (not shown) and one or more memory architectures (not shown) included within ACI compute system 12. Examples of storage device 16 may include but are not limited to: a hard disk drive; a RAID device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g., IO request 20) may be sent from ambient cooperative intelligence process 10s, ambient cooperative intelligence process 10c1, ambient cooperative intelligence process 10c2, ambient cooperative intelligence process 10c3 and/or ambient cooperative intelligence process 10c4 to ACI compute system 12. Examples of IO request 20 may include but are not limited to data write requests (i.e., a request that content be written to ACI compute system 12) and data read requests (i.e., a request that content be read from ACI compute system 12).

The instruction sets and subroutines of ambient cooperative intelligence process 10c1, ambient cooperative intelligence process 10c2, ambient cooperative intelligence process 10c3 and/or ambient cooperative intelligence process 10c4, which may be stored on storage devices 20, 22, 24, 26 (respectively) coupled to ACI client electronic devices 28, 30, 32, 34 (respectively), may be executed by one or more processors (not shown) and one or more memory architectures (not shown) incorporated into ACI client electronic devices 28, 30, 32, 34 (respectively). Storage devices 20, 22, 24, 26 may include but are not limited to: hard disk drives; optical drives; RAID devices; random-access memories (RAM); read-only memories (ROM), and all forms of flash memory storage devices. Examples of ACI client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACI compute system 12 directly through network 14 or through secondary network 18. Further, ACI compute system 12 may be connected to network 14 through secondary network 18, as illustrated with link line 44.

The various ACI client electronic devices (e.g., ACI client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACI client electronic devices (e.g., ACI client electronic devices 28, 30, 32, 34) may each execute an operating system, examples of which may include but are not limited to Microsoft Windows™, Apple Macintosh™, Redhat Linux™, or a custom operating system, wherein the combination of the various ACI client electronic devices (e.g., ACI client electronic devices 28, 30, 32, 34) and ACI compute system 12 may form ACI system 54, an example of which is the Dragon Ambient eXperience (DAX) system offered by Nuance of Burlington, MA The Ambient Cooperative Intelligence System While ambient cooperative intelligence process 10 will be described below as being utilized to automate the collection and processing of clinical encounter information to generate/store/distribute medical records, this is for illustrative purposes only and is not intended to be a limitation of this disclosure, as other configurations are possible and are considered to be within the scope of this disclosure.

Figure 2:
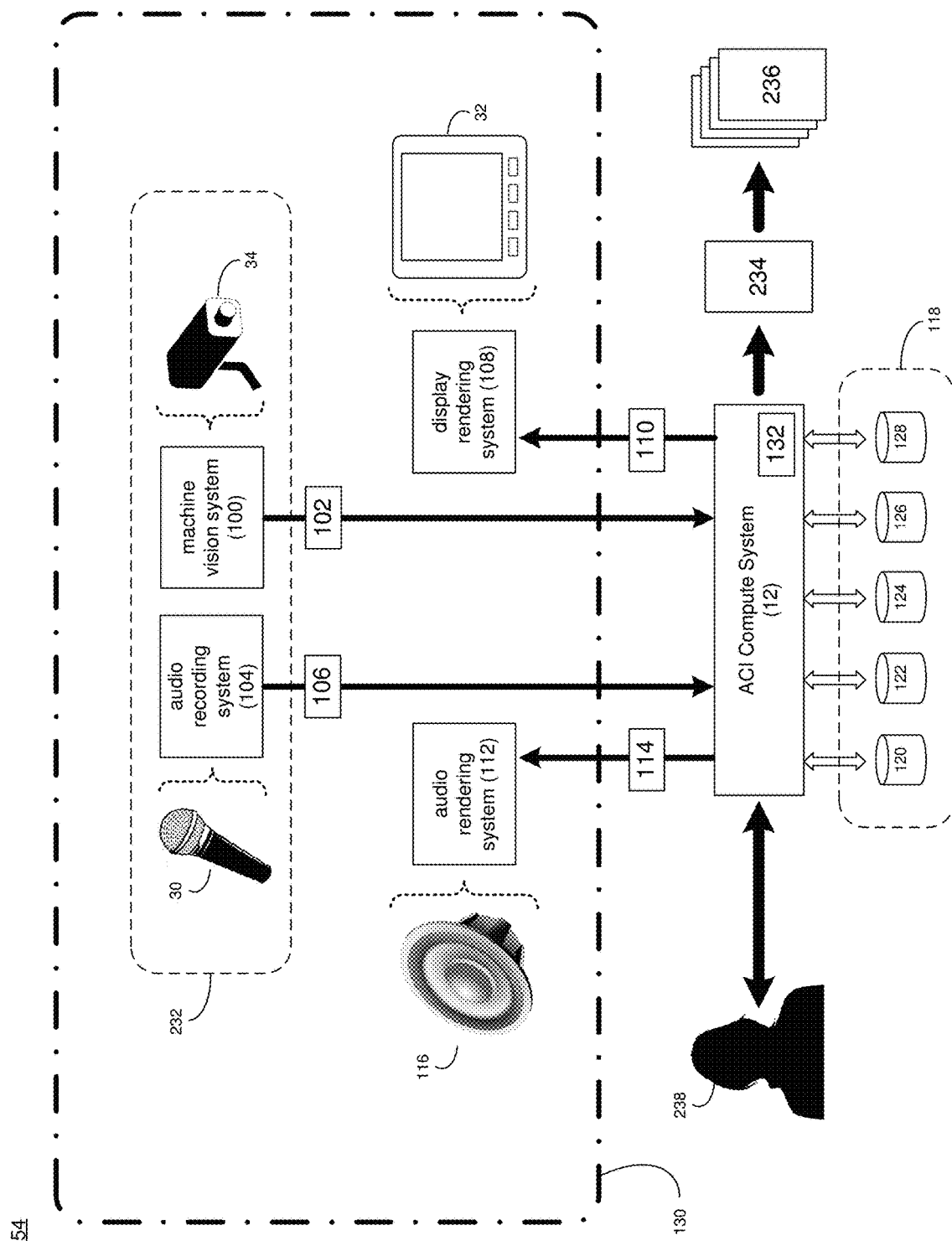
FIG. 2 is a diagrammatic view of an ACI system incorporating the ambient cooperative intelligence compute system of FIG. 1.

Referring also to FIG. 2, there is shown a simplified exemplary embodiment of ACI system 54 that is configured to automate cooperative intelligence. ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively). ACI system 54 may also include: display rendering system 108 configured to render visual information 110; and audio rendering system 112 configured to render audio information 114, wherein ACI compute system 12 may be configured to provide visual information 110 and audio information 114 to display rendering system 108 and audio rendering system 112 (respectively).

Example of machine vision system 100 may include but are not limited to: one or more ACI client electronic devices (e.g., ACI client electronic device 34, examples of which may include but are not limited to an RGB imaging system, an infrared imaging system, an ultraviolet imaging system, a laser imaging system, a SONAR imaging system, a RADAR imaging system, and a thermal imaging system). Examples of audio recording system 104 may include but are not limited to: one or more ACI client electronic devices (e.g., ACI client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device). Examples of display rendering system 108 may include but are not limited to: one or more ACI client electronic devices (e.g., ACI client electronic device 32, examples of which may include but are not limited to a tablet computer, a computer monitor, and a smart television). Examples of audio rendering system 112 may include but are not limited to: one or more ACI client electronic devices (e.g., audio rendering device 116, examples of which may include but are not limited to a speaker system, a headphone system, and an earbud system).

ACI compute system 12 may be configured to access one or more datasources 118 (e.g., plurality of individual datasources 120, 122, 124, 126, 128), examples of which may include but are not limited to one or more of an electronic health record (EHR) datasource, a user profile datasource, a voice print datasource, a voice characteristics datasource (e.g., for adapting the ambient speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource. While in this particular example, five different examples of datasources 118 are shown, this is for illustrative purposes only and is not intended to be a limitation of this disclosure, as other configurations are possible and are considered to be within the scope of this disclosure.

As will be discussed below in greater detail, ACI system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long-term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACI client electronic devices (e.g., ACI client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging system, an ultraviolet imaging system, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACI client electronic devices (e.g., ACI client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACI client electronic devices (e.g., ACI client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACI client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACI compute system 12 may include a plurality of discrete compute systems. As discussed above, ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACI compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Microphone Array

Figure 3:
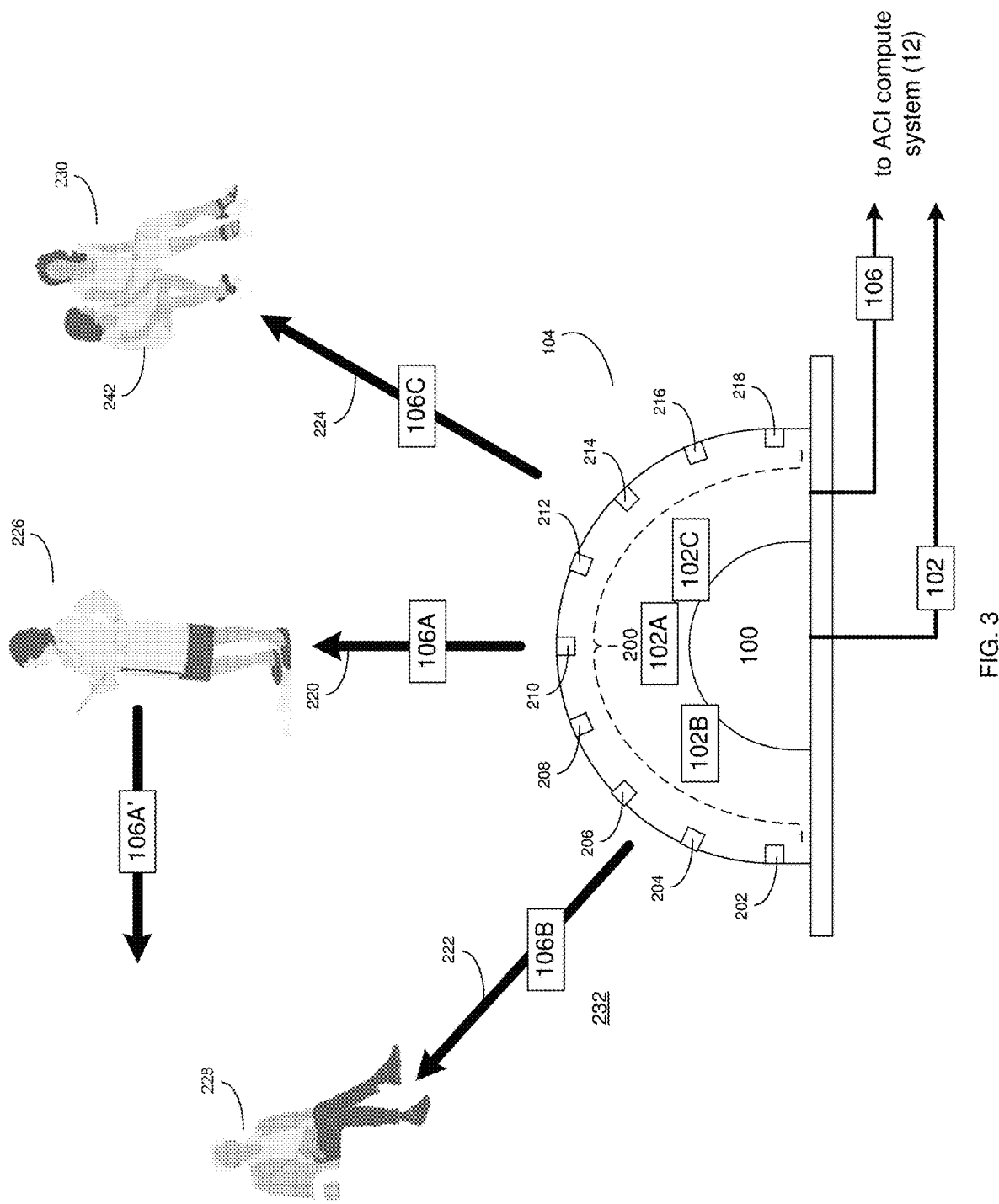
FIG. 3 is a diagrammatic view of a mixed-media ACI device included within the ACI system of FIG. 2.

Referring also to FIG. 3, audio recording system 104 may include microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, ACI system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, ACI system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a quality documentation specialist that performs editing and quality assurance operations) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Further, ACI system 54 and/or audio recording system 104 may be configured to utilize null-steering precoding to cancel interference between speakers and/or noise. As is known in the art, null-steering precoding is a method of spatial signal processing by which a multiple antenna transmitter may null multiuser interference signals in wireless communications, wherein null-steering precoding may mitigate the impact off background noise and unknown user interference. In particular, null-steering precoding may be a method of beamforming for narrowband signals that may compensate for delays of receiving signals from a specific source at different elements of an antenna array. In general and to improve performance of the antenna array, incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACI device 232. For example, mixed-media ACI device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, ACI system 54 may be configured to include a plurality of mixed-media ACI devices (e.g., mixed-media ACI device 232) when the above-described clinical environment is larger or a higher level of resolution is desired.

ACI system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACI device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACI device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACI compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which ACI system 54 (and/or mixed-media ACI device 232) is configured, ACI compute system 12 may be included within mixed-media ACI device 232 or external to mixed-media ACI device 232.

The Ambient Cooperative Intelligence Process

As discussed above, ACI compute system 12 may execute all or a portion of ambient cooperative intelligence process 10, wherein the instruction sets and subroutines of ambient cooperative intelligence process 10 (which may be stored on one or more of e.g., storage devices 16, 20, 22, 24, 26) may be executed by ACI compute system 12 and/or one or more of ACI client electronic devices 28, 30, 32, 34.

Figure 4:
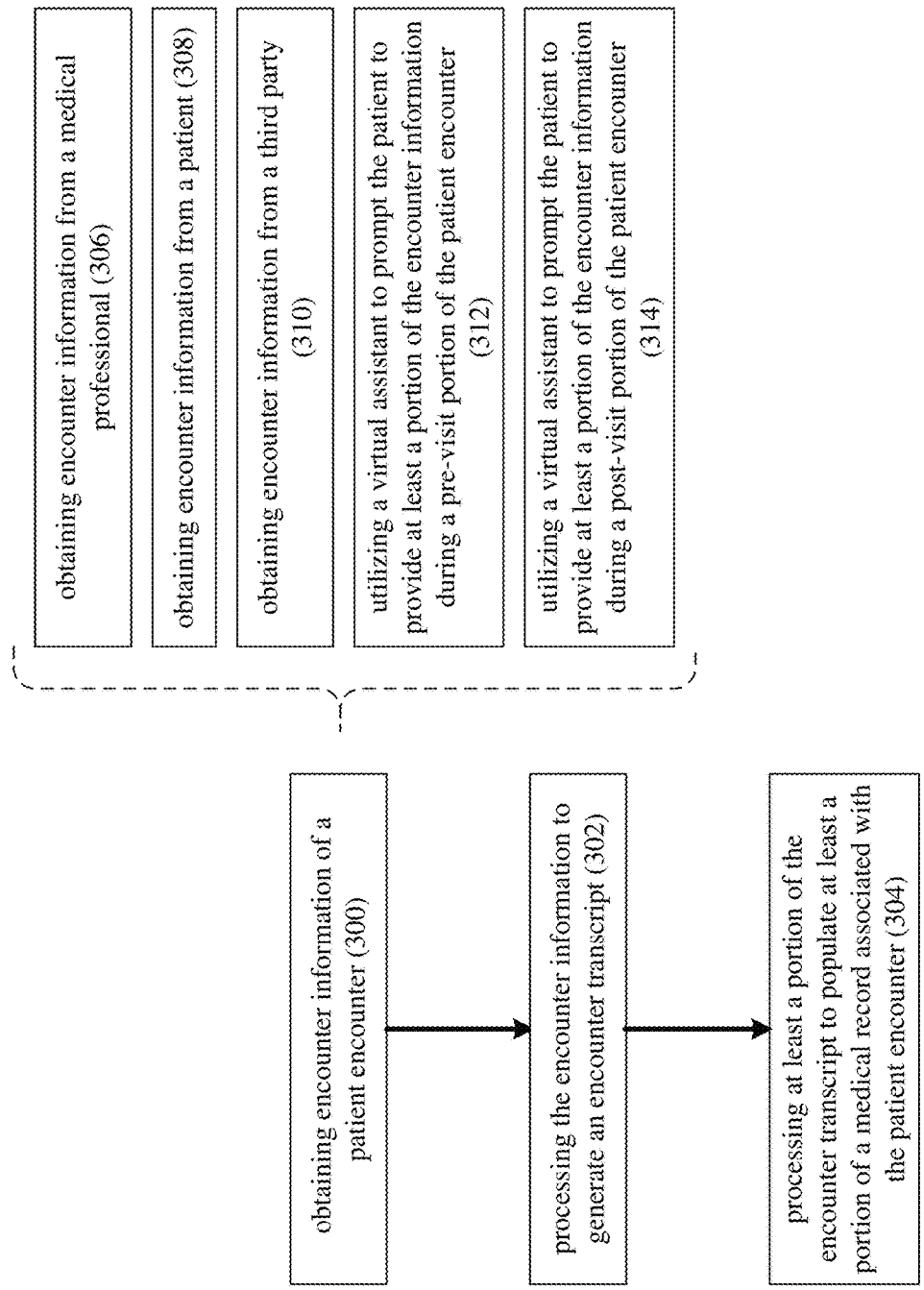
FIG. 4 is a flow chart of one implementation of the ambient cooperative intelligence process of FIG. 1.

As discussed above, ambient cooperative intelligence process 10 may be configured to automate the collection and processing of clinical encounter information to generate/store/distribute medical records. Accordingly and referring also to FIG. 4, ambient cooperative intelligence process 10 may be configured to obtain 300 encounter information (e.g., machine vision encounter information 102 and/or audio encounter information 106) of a patient encounter (e.g., a visit to a doctor's office). Ambient cooperative intelligence process 10 may further be configured to process 302 the encounter information (e.g., machine vision encounter information 102 and/or audio encounter information 106) to generate an encounter transcript (e.g., encounter transcript 234), wherein ambient cooperative intelligence process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe (i.e., a quality documentation specialist that performs editing and quality assurance operations) involved with (or assigned to) the patient encounter (e.g., a visit to a doctor's office) may review encounter transcript 234, a draft of a medical report, and/or medical record 236 to confirm that the same was accurate and/or make corrections to the same. In the event that corrections are made to encounter transcript 234 and/or medical record 236, ambient cooperative intelligence process 10 may utilize these corrections for training/tuning purposes (e.g., to adjust the various profiles associated the participants of the patient encounter) to enhance the future accuracy/efficiency/performance of ambient cooperative intelligence process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, ambient cooperative intelligence process 10 may utilize these corrections for training/tuning purposes (e.g., to adjust the various profiles associated the participants of the patient encounter) to enhance the future accuracy/efficiency/performance of ambient cooperative intelligence process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACI compute system 12 and/or ACI system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACI compute system 12 and/or ACI system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip-reading functionality) may be utilized by ambient cooperative intelligence process 10 to further effectuate the gathering of audio encounter information 106.

Accordingly and when obtaining 300 encounter information (e.g., machine vision encounter information 102 and/or audio encounter information 106), ambient cooperative intelligence process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), ambient cooperative intelligence process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by ambient cooperative intelligence process 10.

When ambient cooperative intelligence process 10 obtains 300 the encounter information, ambient cooperative intelligence process 10 may utilize 312 a medical virtual assistant (e.g., medical virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office). Generally speaking, a pre-visit portion (e.g., a patient intake portion) of the patient encounter (e.g., encounter participant 228 visiting the doctor's office) is the portion of the patient encounter that occurs before the consultation portion (i.e., the portion of the patient encounter in which the patient (e.g., encounter participant 228) meets with the medical professional (e.g., encounter participant 226).

Further and when ambient cooperative intelligence process 10 obtains 300 encounter information, ambient cooperative intelligence process 10 may utilize 314 a medical virtual assistant (e.g., medical virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office). Generally speaking, a post-visit portion (e.g., a patient follow-up portion) of the patient encounter (e.g., encounter participant 228 visiting the doctor's office) is the portion of the patient encounter that occurs after the consultation portion (i.e., the portion of the patient encounter in which the patient (e.g., encounter participant 228) meets with the medical professional (e.g., encounter participant 226).

Automated Transcript Generation

Ambient cooperative intelligence process 10 may be configured to process the encounter information (e.g., machine vision encounter information 102 and/or audio encounter information 106) to generate encounter transcript 234 that may be automatically formatted and punctuated.

Figure 5:
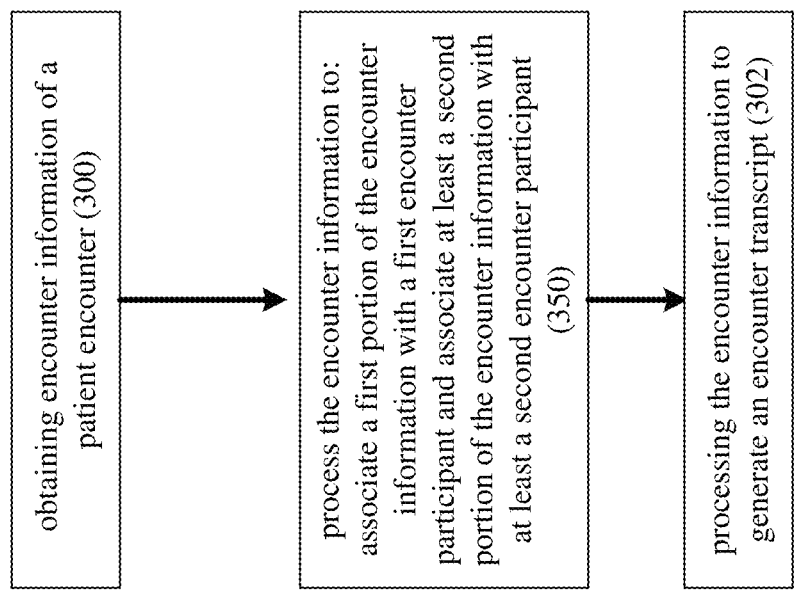
FIG. 5 is a flow chart of another implementation of the ambient cooperative intelligence process of FIG. 1.

Accordingly and referring also to FIG. 5, ambient cooperative intelligence process 10 may be configured to obtain 300 encounter information (e.g., machine vision encounter information 102 and/or audio encounter information 106) of a patient encounter (e.g., a visit to a doctor's office).

Ambient cooperative intelligence process 10 may process 350 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, ACI system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein ACI system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, ACI system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly, ambient cooperative intelligence process 10 may process 350 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 350 the encounter information (e.g., audio encounter information 106A, 106B, 106C), ambient cooperative intelligence process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 350, ambient cooperative intelligence process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B. 106C).

Automated Role Assignment

Ambient cooperative intelligence process 10 may be configured to automatically define roles for the encounter participants (e.g., encounter participants 226, 228, 230) in the patient encounter (e.g., a visit to a doctor's office).

Figure 6:
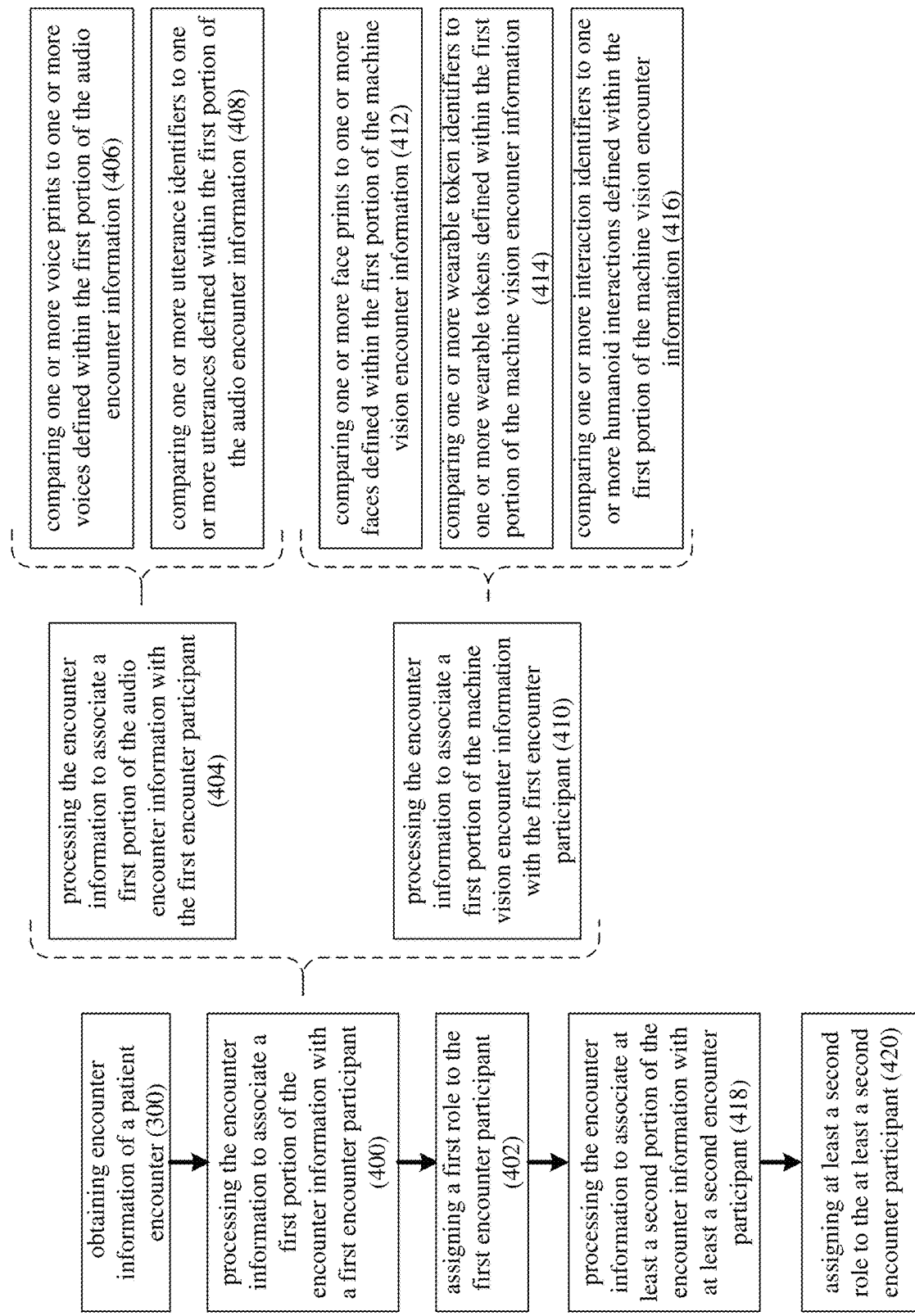
FIG. 6 is a flow chart of another implementation of the ambient cooperative intelligence process of FIG. 1.

Accordingly and referring also to FIG. 6, ambient cooperative intelligence process 10 may be configured to obtain 300 encounter information (e.g., machine vision encounter information 102 and/or audio encounter information 106) of a patient encounter (e.g., a visit to a doctor's office).

Ambient cooperative intelligence process 10 may then process 400 the encounter information (e.g., machine vision encounter information 102 and/or audio encounter information 106) to associate a first portion of the encounter information with a first encounter participant (e.g., encounter participant 226) and assign 402 a first role to the first encounter participant (e.g., encounter participant 226).

When processing 400 the encounter information (e.g., machine vision encounter information 102 and/or audio encounter information 106) to associate the first portion of the encounter information with the first encounter participant (e.g., encounter participant 226), ambient cooperative intelligence process 10 may process 404 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 404 the encounter information (e.g., machine vision encounter information 102 and/or audio encounter information 106) to associate the first portion of the audio encounter information (e.g., audio encounter information 106A) with the first encounter participant (e.g., encounter participant 226), ambient cooperative intelligence process 10 may compare 406 one or more voice prints (defined within voice print datasource) to one or more voices defined within the first portion of the audio encounter information (e.g., audio encounter information 106A); and may compare 408 one or more utterance identifiers (defined within utterance datasource) to one or more utterances defined within the first portion of the audio encounter information (e.g., audio encounter information 106A); wherein comparisons 406, 408 may allow ambient cooperative intelligence process 10 to assign 402 a first role to the first encounter participant (e.g., encounter participant 226). For example, if the identity of encounter participant 226 can be defined via voice prints, a role for encounter participant 226 may be assigned 402 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 402.

When processing 400 the encounter information (e.g., machine vision encounter information 102 and/or audio encounter information 106) to associate the first portion of the encounter information with the first encounter participant (e.g., encounter participant 226), ambient cooperative intelligence process 10 may process 410 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 410 the encounter information (e.g., machine vision encounter information 102 and/or audio encounter information 106) to associate the first portion of the machine vision encounter information (e.g., machine vision encounter information 102A) with the first encounter participant (e.g., encounter participant 226), ambient cooperative intelligence process 10 may compare 412 one or more face prints (defined within face print datasource) to one or more faces defined within the first portion of the machine vision encounter information (e.g., machine vision encounter information 102A); compare 414 one or more wearable token identifiers (defined within wearable token identifier datasource) to one or more wearable tokens defined within the first portion of the machine vision encounter information (e.g., machine vision encounter information 102A); and compare 416 one or more interaction identifiers (defined within interaction identifier datasource) to one or more humanoid interactions defined within the first portion of the machine vision encounter information (e.g., machine vision encounter information 102A); wherein comparisons 412, 414, 416 may allow ambient cooperative intelligence process 10 to assign 402 a first role to the first encounter participant (e.g., encounter participant 226). For example, if the identity of encounter participant 226 can be defined via face prints, a role for encounter participant 226 may be assigned 402 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 402. Additionally, if an interaction made by encounter participant 226 corresponds to the type of interaction that is made by a doctor, the existence of this interaction may allow a role for encounter participant 226 to be assigned 402.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, travelling to and/or from monitored space 130, and/or outside of monitored space 130 (e.g., at home).

Additionally, ambient cooperative intelligence process 10 may process 418 the encounter information (e.g., machine vision encounter information 102 and/or audio encounter information 106) to associate at least a second portion of the encounter information with at least a second encounter participant; and may assign 420 at least a second role to the at least a second encounter participant.

Specifically, ambient cooperative intelligence process 10 may process 418 the encounter information (e.g., machine vision encounter information 102 and/or audio encounter information 106) to associate at least a second portion of the encounter information with at least a second encounter participant. For example, ambient cooperative intelligence process 10 may process 418 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, ambient cooperative intelligence process 10 may assign 420 at least a second role to the at least a second encounter participant. For example, ambient cooperative intelligence process 10 may assign 420 a role to encounter participants 228, 230.

Automated Movement Tracking

Ambient cooperative intelligence process 10 may be configured to track the movement and/or interaction of humanoid shapes within the monitored space (e.g., monitored space 130) during the patient encounter (e.g., a visit to a doctor's office) so that e.g., the ambient cooperative intelligence process 10 knows when encounter participants (e.g., one or more of encounter participants 226, 228, 230) enter, exit r cross paths within monitored space 130.

Figure 7:
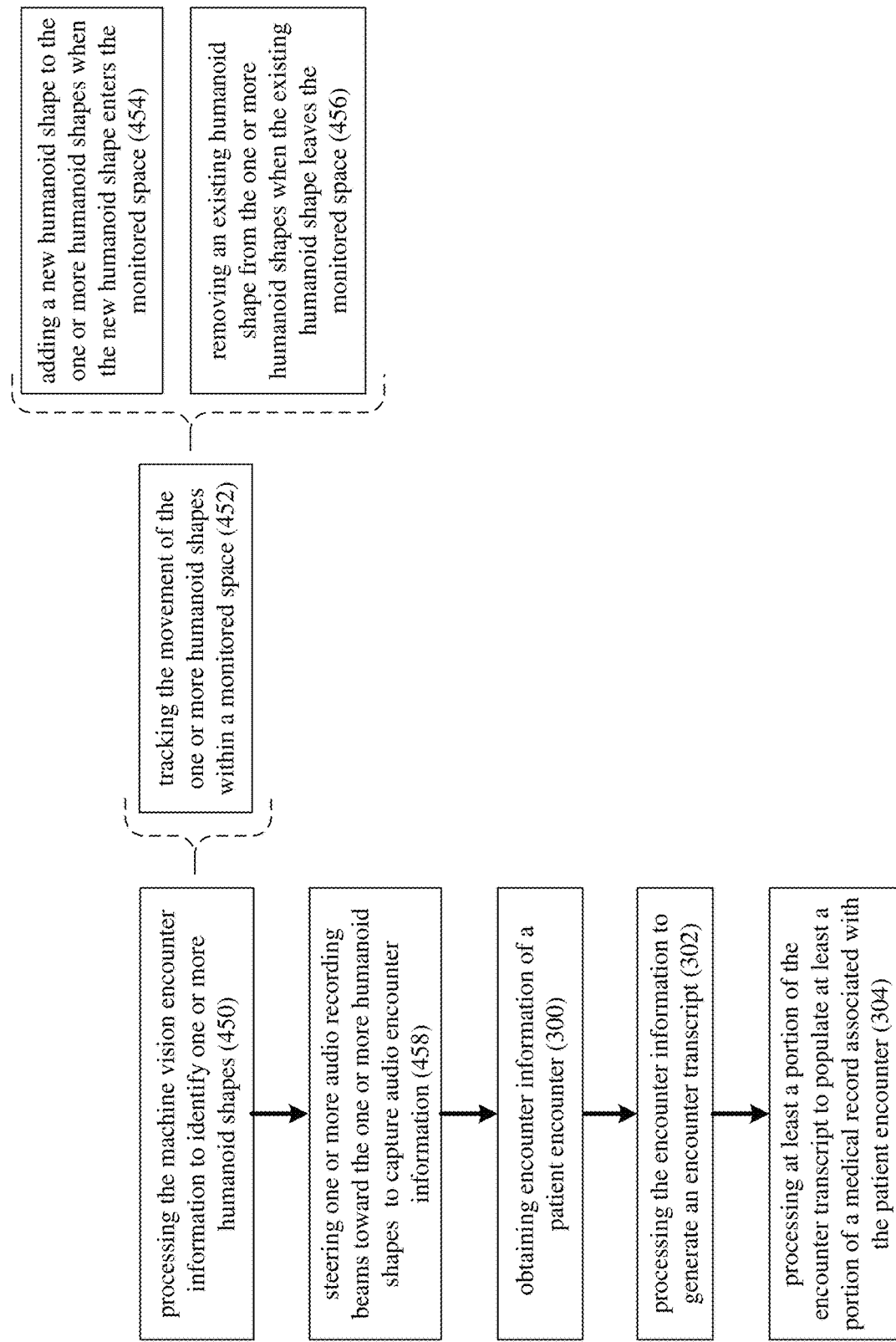
FIG. 7 is a flow chart of another implementation of the ambient cooperative intelligence process of FIG. 1.

Accordingly and referring also to FIG. 7, ambient cooperative intelligence process 10 may process 450 the machine vision encounter information (e.g., machine vision encounter information 102) to identify one or more humanoid shapes. As discussed above, examples of machine vision system 100 generally (and ACI client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACI client electronic device 34 includes a visible light imaging system (e.g., an RGB imaging system), ACI client electronic device 34 may be configured to monitor various objects within monitored space 130 by recording motion video in the visible light spectrum of these various objects. When ACI client electronic device 34 includes an invisible light imaging system (e.g., a laser imaging system, an infrared imaging system and/or an ultraviolet imaging system), ACI client electronic device 34 may be configured to monitor various objects within monitored space 130 by recording motion video in the invisible light spectrum of these various objects. When ACI client electronic device 34 includes an X-ray imaging system, ACI client electronic device 34 may be configured to monitor various objects within monitored space 130 by recording energy in the X-ray spectrum of these various objects. When ACI client electronic device 34 includes a SONAR imaging system, ACI client electronic device 34 may be configured to monitor various objects within monitored space 130 by transmitting soundwaves that may be reflected off of these various objects. When ACI client electronic device 34 includes a RADAR imaging system, ACI client electronic device 34 may be configured to monitor various objects within monitored space 130 by transmitting radio waves that may be reflected off of these various objects. When ACI client electronic device 34 includes a thermal imaging system, ACI client electronic device 34 may be configured to monitor various objects within monitored space 130 by tracking the thermal energy of these various objects.

As discussed above, ACI compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly and when processing 450 the machine vision encounter information (e.g., machine vision encounter information 102) to identify one or more humanoid shapes, ambient cooperative intelligence process 10 may be configured to compare the humanoid shapes defined within one or more datasources 118 to potential humanoid shapes within the machine vision encounter information (e.g., machine vision encounter information 102).

When processing 450 the machine vision encounter information (e.g., machine vision encounter information 102) to identify one or more humanoid shapes, ambient cooperative intelligence process 10 may track 452 the movement of the one or more humanoid shapes within the monitored space (e.g., monitored space 130). For example and when tracking 452 the movement of the one or more humanoid shapes within monitored space 130, ambient cooperative intelligence process 10 may add 454 a new humanoid shape to the one or more humanoid shapes when the new humanoid shape enters the monitored space (e.g., monitored space 130) and/or may remove 456 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, ambient cooperative intelligence process 10 may add 454 encounter participant 242 to the one or more humanoid shapes being tracked 452 when the new humanoid shape (i.e., encounter participant 242) enters monitored space 130. Further, assume that the lab technician (e.g., encounter participant 242) leaves monitored space 130 after chatting with encounter participant 230. Therefore, ambient cooperative intelligence process 10 may remove 456 encounter participant 242 from the one or more humanoid shapes being tracked 452 when the humanoid shape (i.e., encounter participant 242) leaves monitored space 130.

Also and when tracking 452 the movement of the one or more humanoid shapes within monitored space 130, ambient cooperative intelligence process 10 may monitor the trajectories of the various humanoid shapes within monitored space 130. Accordingly, assume that when leaving monitored space 130, encounter participant 242 walks in front of (or behind) encounter participant 226. As ambient cooperative intelligence process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by ambient cooperative intelligence process 10.

Ambient cooperative intelligence process 10 may be configured to obtain 300 the encounter information of the patient encounter (e.g., a visit to a doctor's office), which may include machine vision encounter information 102 (in the manner described above) and/or audio encounter information 106.

Ambient cooperative intelligence process 10 may steer 458 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically and as discussed above, ambient cooperative intelligence process 10 (via ACI system 54 and/or audio recording system 104) may utilize one or more of the discrete audio acquisition devices (e.g., audio acquisition devices 202, 204, 206, 208, 210, 212, 214, 216, 218) to form an audio recording beam. For example, ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Once obtained, ambient cooperative intelligence process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Telehealth (Remote Encounters)
System Overview

Regular access to medical professionals is of paramount importance for people maintaining their health. Accordingly, it has been shown that annual physicals are instrumental to maintaining a patient's health. Further and in the event of an illness, it is important that a medical professional is engaged in a timely fashion. Unfortunately, such medical professionals are often not timely engaged. For example, it is often difficult for people to travel to see a doctor. Further and especially when a specialist is needed, a significant amount of travel may be required in order to visit with such a medical professional. Accordingly, telehealth visits may solve some of these issues by allowing a patient to visit with a doctor without having to actually travel to the doctor's office.

Figure 8:
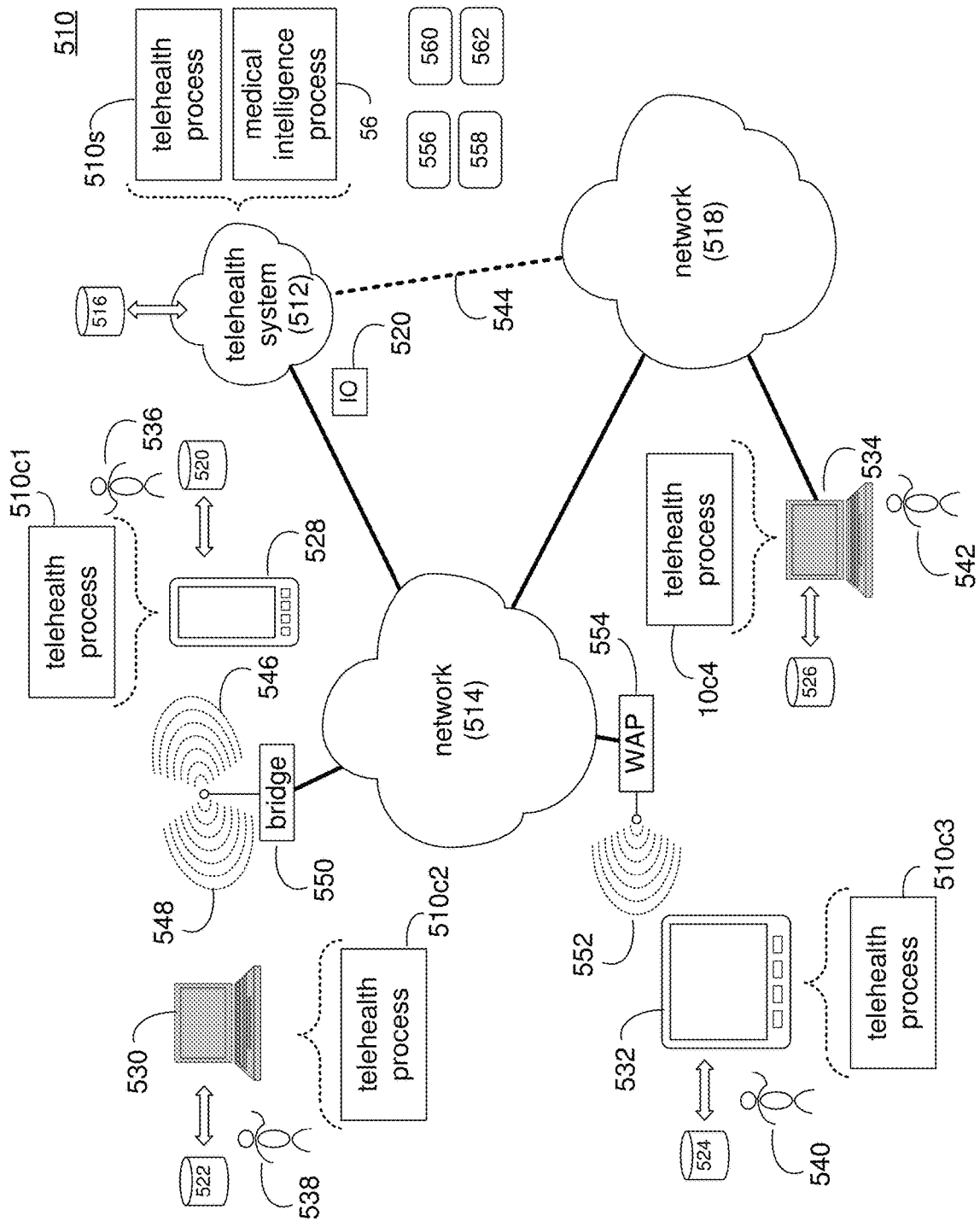
FIG. 8 is a diagrammatic view of a telehealth system, a telehealth process and a medical intelligence process coupled to a distributed computing network.

Referring to FIG. 8, there is shown telehealth process 510. As will be discussed below in greater detail, telehealth process 510 may be configured to effectuate a telehealth visit between a medical professional and a patient.

Telehealth process 510 may be implemented as a server-side process, a client-side process, or a hybrid server-side/client-side process. For example, telehealth process 510 may be implemented as a purely server-side process via telehealth process 510s. Alternatively, telehealth process 510 may be implemented as a purely client-side process via one or more of telehealth process 510c1, telehealth process 510c2, telehealth process 510c3, and telehealth process 510c4. Alternatively still, telehealth process 510 may be implemented as a hybrid server-side/client-side process via telehealth process 510s in combination with one or more of telehealth process 510c1, telehealth process 510c2, telehealth process 510c3, and telehealth process 510c4.

Accordingly, telehealth process 510 as used in this disclosure may include any combination of telehealth process 510s, telehealth process 510c1, telehealth process 510c2, telehealth process 510c3, and telehealth process 510c4.

Telehealth process 510s may be a server application and may reside on and may be executed by telehealth system 512, which may be connected to network 514 (e.g., the Internet or a local area network). Telehealth system 512 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, one or more software applications, one or more software platforms, a cloud-based computational system, and a cloud-based storage platform.

As is known in the art, a SAN may include one or more of a personal computer, a server computer, a series of server computers, a mini computer, a mainframe computer, a RAID device and a NAS system. The various components of telehealth system 512 may execute one or more operating systems, examples of which may include but are not limited to: Microsoft Windows Server™, Redhat Linux™, Unix, or a custom operating system, for example.

The instruction sets and subroutines of telehealth process 510s, which may be stored on storage device 516 coupled to telehealth system 512, may be executed by one or more processors (not shown) and one or more memory architectures (not shown) included within telehealth system 512. Examples of storage device 516 may include but are not limited to: a hard disk drive; a RAID device; a random-access memory (RAM); a read-only memory (ROM); and all forms of flash memory storage devices.

Network 514 may be connected to one or more secondary networks (e.g., network 518), examples of which may include but are not limited to: a local area network; a wide area network; or an intranet, for example.

Various IO requests (e.g., IO request 520) may be sent from telehealth process 510s, telehealth process 510c1, telehealth process 510c2, telehealth process 510c3 and/or telehealth process 510c4 to telehealth system 512. Examples of IO request 520 may include but are not limited to data write requests (i.e., a request that content be written to data acquisition system 512) and data read requests (i.e., a request that content be read from data acquisition system 512).

The instruction sets and subroutines of telehealth process 510c1, telehealth process 510c2, telehealth process 510c3 and/or telehealth process 510c4, which may be stored on storage devices 520, 522, 524, 526 (respectively) coupled to client electronic devices 528, 530, 532, 534 (respectively), may be executed by one or more processors (not shown) and one or more memory architectures (not shown) incorporated into client electronic devices 528, 530, 532, 534 (respectively). Storage devices 520, 522, 524, 526 may include but are not limited to: hard disk drives; optical drives; RAID devices; random access memories (RAM); read-only memories (ROM), and all forms of flash memory storage devices.

Examples of client electronic devices 528, 530, 532, 534 may include, but are not limited to, data-enabled, cellular telephone 528, laptop computer 530, tablet computer 532, laptop computer 534, a notebook computer (not shown), a server computer (not shown), a gaming console (not shown), a smart television (not shown), and a dedicated network device (not shown). Client electronic devices 528, 530, 532, 534 may each execute an operating system, examples of which may include but are not limited to Microsoft Windows™, Android™, WebOS™, iOS™, Redhat Linux™, or a custom operating system.

Users 536, 538, 540, 542 may access telehealth process 510 directly through network 514 or through secondary network 518. Further, telehealth process 510 may be connected to network 514 through secondary network 518, as illustrated with link line 544.

The various client electronic devices (e.g., client electronic devices 528, 530, 532, 534) may be directly or indirectly coupled to network 514 (or network 518). For example, data-enabled, cellular telephone 528 and laptop computer 530 are shown wirelessly coupled to network 514 via wireless communication channels 546, 548 (respectively) established between data-enabled, cellular telephone 528, laptop computer 530 (respectively) and cellular network/bridge 550, which is shown directly coupled to network 514. Further, tablet computer 532 is shown wirelessly coupled to network 514 via wireless communication channel 552 established between tablet computer 532 and wireless access point (i.e., WAP) 554, which is shown directly coupled to network 514. WAP 554 may be, for example, an IEEE 802.11a, 802.11b, 802.11g, 802.11n, Wi-Fi, and/or Bluetooth device that is capable of establishing wireless communication channel 552 between tablet computer 532 and WAP 554. Additionally, laptop computer 534 is shown directly coupled to network 518 via a hardwired network connection.

The Telehealth System

Figure 9:
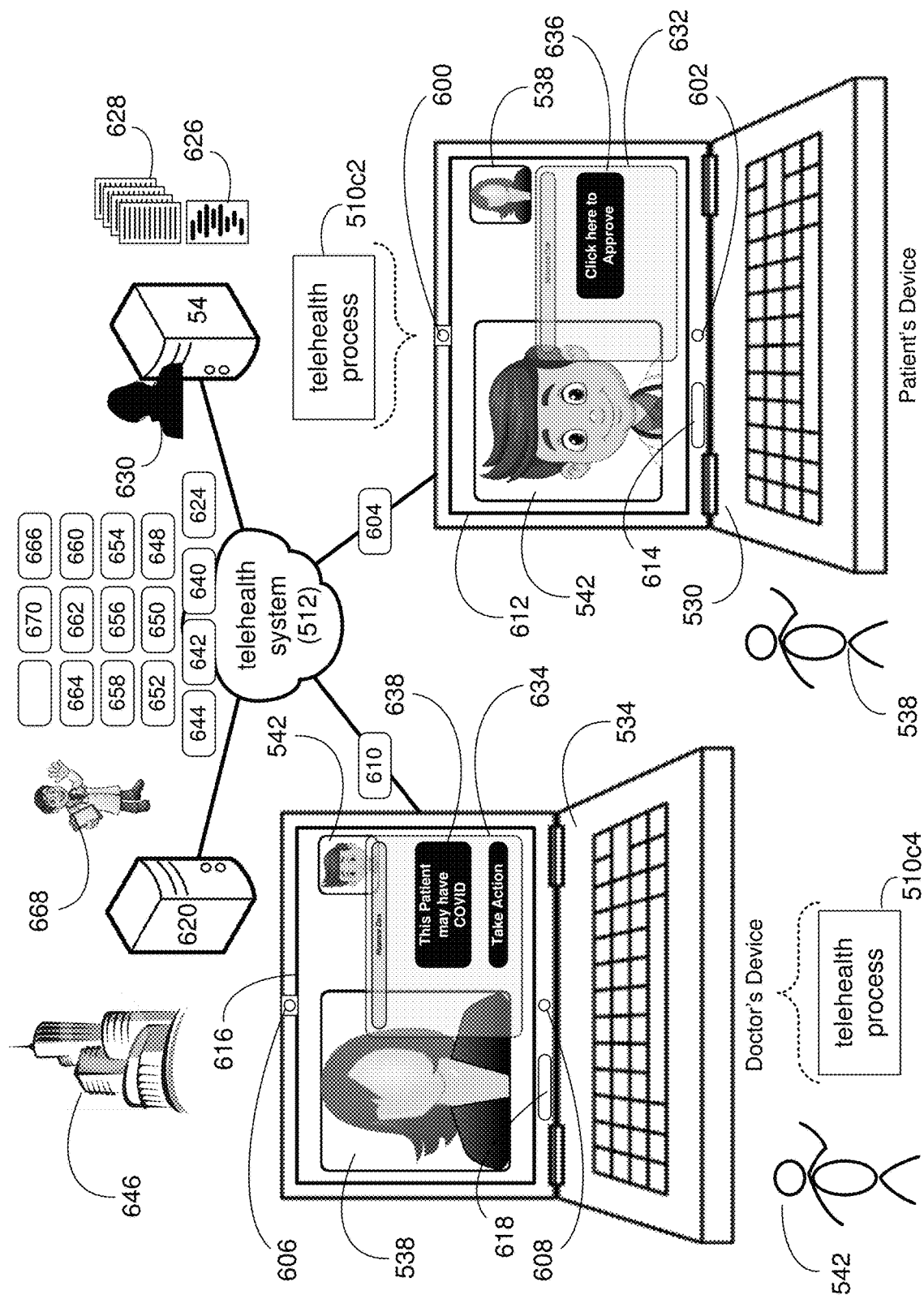
FIG. 9 is a diagrammatic view of the telehealth system of FIG. 8.

Referring also to FIG. 9 and as discussed above, telehealth process 510 in combination with telehealth system 512 may be configured to enable telehealth medical encounters between a medical professional and a patient. While the following illustrative example concerns a telehealth medical encounter between a single doctor and a single patient, this is for illustrative purposes only and is not intended to be a limitation of this disclosure, as other configurations are possible and are considered to be within the scope of this disclosure. For example, telehealth process 510 in combination with telehealth system 512 may establish a telehealth medical encounter between a team of medical professionals, a patient and one or more interested parties (e.g., patients, relatives, guardians, etc.).

As is known in the art, telehealth is the distribution of health-related services and information via electronic information and telecommunication technologies. Telehealth medical encounters may allow long-distance patient and clinician contact, care, advice, reminders, education, intervention, monitoring, and remote admissions. Telemedicine may sometimes be used as a synonym, or may be used in a more limited sense to describe remote clinical services, such as diagnosis and monitoring. When rural settings, lack of transport, a lack of mobility, decreased funding, or a lack of staff restrict access to care; telehealth may bridge the gap, as well as provide: distance-learning, meetings, supervision, and presentations between practitioners; online information and health data management; and healthcare system integration. Telehealth may include two clinicians discussing a case over video conference; a robotic surgery occurring through remote access; physical therapy performed via digital monitoring instruments, live feed and application combinations; tests being forwarded between facilities for interpretation by a higher specialist; home monitoring through continuous sending of patient health data; client to practitioner online conference; or even videophone interpretation during a consult.

For example, assume that a patient (e.g., user 538) wishes to meet with a doctor (e.g., user 542). However and for various reasons (e.g., a pandemic, a geographic distance, lack of geographically-proximate practitioners, etc.), the patient (e.g., user 538) cannot physically meet with the doctor (e.g., user 542). Therefore, telehealth process 510 in combination with telehealth system 512 may enable the patient (e.g., user 538) to virtually meet with the doctor (e.g., user 542) via a telehealth medical encounter.

Specifically, the patient (e.g., user 538) may utilize their client electronic device (e.g., laptop computer 530) and telehealth process 510c2 to participate in a telehealth medical encounter with the doctor (e.g., user 542), who will utilize their client electronic device (e.g., laptop computer 534) and telehealth process 510c4.

The client electronic device (e.g., laptop computer 530) of the patient (e.g., user 538) may include video camera 600 and microphone 602 to generate audio/video stream (e.g., AV stream 604) that may be provided via telehealth system 512 to the client electronic device (e.g., laptop computer 534) of the doctor (e.g., user 542). Additionally, the client electronic device (e.g., laptop computer 534) of the doctor (e.g., user 542) may include video camera 606 and microphone 608 to generate audio/video stream (e.g., AV stream 610) that may be provided via telehealth system 512 to the client electronic device (e.g., laptop computer 530) of the patient (e.g., user 538).

Telehealth process 510 (generally) and telehealth process 510c2 (specifically) may render user interface 612 on the client electronic device (e.g., laptop computer 530) of the patient (e.g., user 538). User interface 612 may render a smaller-size video feed of the patient (e.g., user 538), which is obtained from video camera 600 and allows the patient (e.g., user 538) to monitor the way that they appear within the telehealth medical encounter. Further, user interface 612 may render a larger-size video feed of the doctor (e.g., user 542) as well as an audio signal from the doctor (e.g., user 542) on speaker assembly 614, both of which are obtained from AV stream 610 and allow the patient (e.g., user 538) to see, hear and interact with the doctor (e.g., user 542).

Telehealth process 510 (generally) and telehealth process 510c4 (specifically) may render user interface 616 on the client electronic device (e.g., laptop computer 534) of the doctor (e.g., user 542). User interface 616 may render a smaller-size video feed of the doctor (e.g., user 542), which is obtained from video camera 606 and allows the doctor (e.g., user 542) to monitor the way that they appear within the telehealth medical encounter. Further, user interface 616 may render a larger-size video feed of the patient (e.g., user 538) as well as an audio signal from the patient (e.g., user 538) on speaker assembly 618, both of which are obtained from AV stream 604 and allow the doctor (e.g., user 542) to see, hear and interact with the patient (e.g., user 538).

Telehealth system 512 may be coupled to one or more collaborating systems (e.g., collaborating system 620), examples of which may include but are not limited to a collaborating system executing a PACS system and a collaborating system executing an EHR system.

As is known in the art, a PACS (Picture Archiving and Communication System) system is a medical imaging technology that provides economical storage and convenient access to images from multiple modalities (source machine types). Electronic images and reports may be transmitted digitally via PACS; thus eliminating the need to manually file, retrieve and/or transport film jackets. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM.

As is known in the art, an EHR (Electronic Health Record) system is a systematized collection of patient and population electronically stored health information in a digital format. These records may be shared across different health care settings, wherein records maybe shared through network-connected, enterprise-wide information systems or other information networks and exchanges. An EHR system may define a range of data, including demographics, medical histories, medications and allergies, immunization status, laboratory test results, radiology images, vital signs, personal statistics, and billing information.

Accordingly and through the use of such a PAX system and an EHR system, the doctor (e.g., user 42) may access and review medical images and electronic health records associated with the patient (e.g., user 38).

Telehealth system 512 may also be coupled to an ambient cooperative intelligence system (e.g., ACI system 54 described above). ACI system 54 may be configured to automate the gathering and processing of clinical encounter information (e.g., gathered encounter information 624) associated with a patient encounter (e.g., the telehealth medical encounter between the patient (e.g., user 538) and the doctor (e.g., user 542)).

As discussed above, ACI system 54 may be configured to process the encounter information (e.g., gathered encounter information 624) to generate an encounter transcript (e.g., encounter transcript 626), wherein ACI system 54 may then process at least a portion of the encounter transcript (e.g., encounter transcript 626) to populate at least a portion of a medical record (e.g., medical record 628) associated with the patient encounter (e.g., the telehealth medical encounter between the patient (e.g., user 538) and the doctor (e.g., user 542)). Accordingly, ACI system 54 may gather clinical encounter information (e.g., gathered encounter information 624) associated with the telehealth medical encounter between the patient (e.g., user 538) and the doctor (e.g., user 542) to generate/store/distribute medical records (e.g., medical records 628) for the patient (e.g., user 538).

As also discussed above, ACI system 54 may be configured to process the encounter information (e.g., gathered encounter information 624) to assign roles to the participants of the meeting. For example, ACI system 54 may listen for specific phases stated by the participants, such as "Hello, I am Dr. Jones . . . what brings you to the office today?" (which would indicate that the person speaking is a doctor) or "Hello Doctor, I am having a hard time breathing for the past couple of weeks" (which would indicate that the person speaking is a patient). Additionally/alternatively, ACI system 54 may monitor the network connection from which the participants are accessing telehealth system 512. For example, the client electronic device (e.g., laptop computer 534) of the doctor (e.g., user 542) may access telehealth system 512 from a local IP address (e.g., 192.xxx.yyy.zzz), while the client electronic device (e.g., laptop computer 530) of the patient (e.g., user 538) may access telehealth system 512 from a remote IP address (e.g., 113.xxx.yyy.zzz). Accordingly, ACI system 54 may process gathered encounter information 624 to assign a role of "doctor" to user 542 and assign the role of "patient" to user 538.

ACI system 54 may utilize natural language processing and artificial intelligence to process data included within the encounter transcript (e.g., encounter transcript 626) and/or data included within AV streams 604, 610. For example and as will be discussed below, ACI system 54 may monitor the meeting between the patient (e.g., user 538) and the doctor (e.g., user 542) during the above-described telehealth medical encounter.

As is known in the art, natural language processing (NLP) is a subfield of linguistics, computer science, and artificial intelligence concerned with the interactions between computers and human language, in particular how to program computers to process and analyze large amounts of natural language data. The goal is a computer capable of "understanding" the contents of documents, including the contextual nuances of the language within them. The technology may then accurately extract information and insights contained in the documents as well as categorize and organize the documents themselves.

As is known in the art, artificial intelligence (AI) and/or machine learning (ML) is the study of computer algorithms that improve automatically through experience and by the use of data. Artificial intelligence and machine learning algorithms may build a model based on sample data (known as "training data") in order to make predictions or decisions without being explicitly programmed to do so. Artificial intelligence and machine learning algorithms may be used in a wide variety of applications, such as in medicine, email filtering, speech recognition, and computer vision, wherein it may be difficult or unfeasible to develop conventional algorithms to perform the needed tasks. Artificial intelligence and machine learning may involve computers discovering how they can perform tasks without being explicitly programmed to do so (e.g., where computers learn from sample data (known as "training data") how to carry out certain tasks.

As is known in the art, a machine learning system or model may generally include an algorithm (or combination of algorithms) that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

The Telehealth Process

Figure 10:
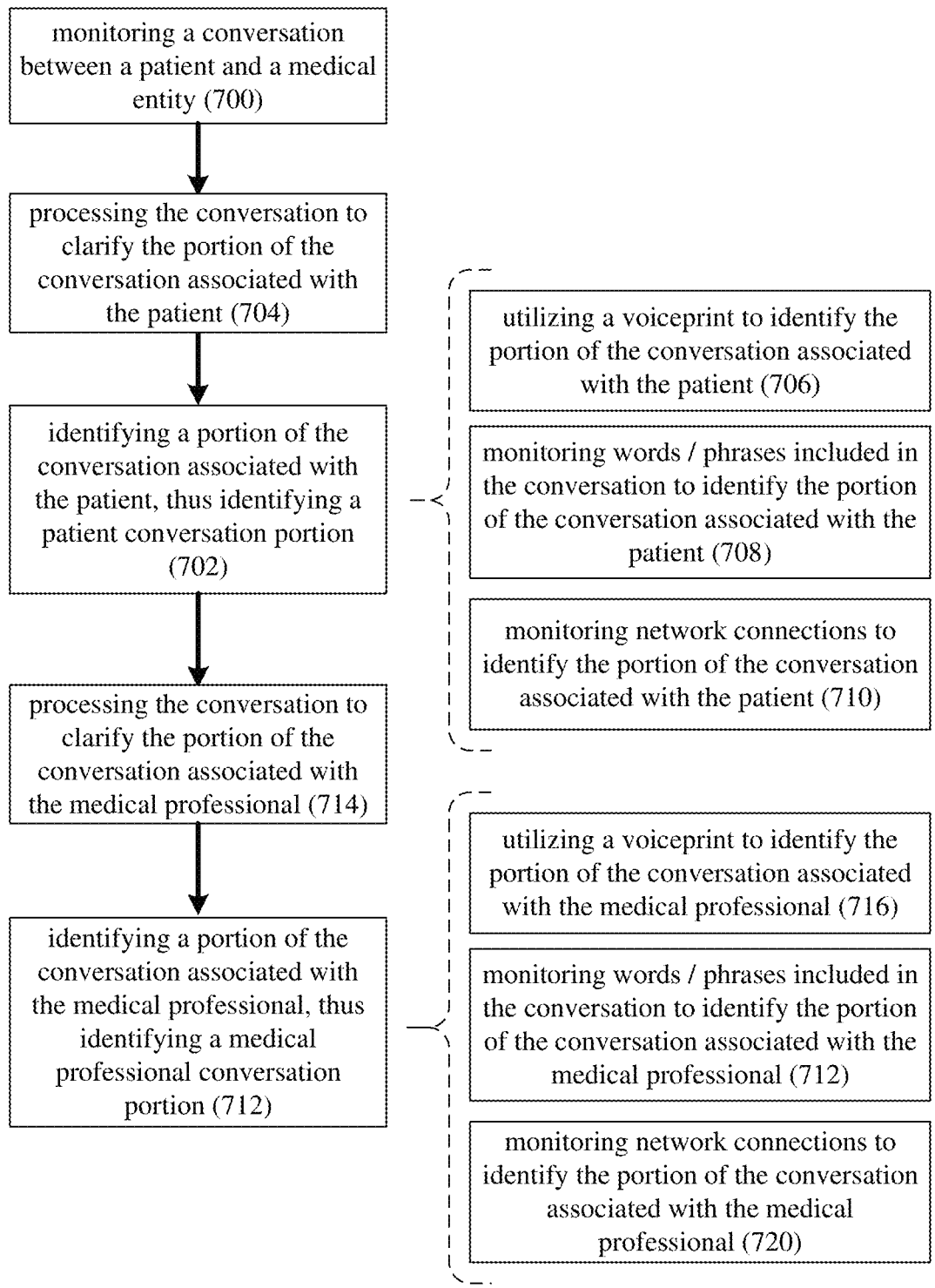
FIG. 10 is a flow chart of the telehealth process of FIG. 8.

Referring also to FIG. 10, telehealth process 510 (alone or in conjunction with ACI system 54) may monitor 700 a meeting (e.g., the above-described telehealth medical encounter) between a patient (e.g., user 538) and a medical entity. Examples of this medical entity may include but are not limited to: a medical professional (e.g., user 542) and a medical virtual assistant (e.g., medical virtual assistant 630). As is known in the art, a virtual assistant (e.g., medical virtual assistant 630) is a software agent that may perform tasks or services for an individual based upon commands or questions. The term "chatbot" is sometimes used to refer to virtual assistants generally or specifically to those accessed via online chat. Some virtual assistants may interpret human speech and respond via synthesized voices. Users may ask their virtual assistant questions, control home automation devices and media playback via voice, and manage other basic tasks such as email, to-do lists, and calendars with verbal commands.

When monitoring 700 the meeting (e.g., the above-described telehealth medical encounter) between (in this example) the patient (e.g., user 538) and the medical entity, natural language processing and artificial intelligence may be utilized to process data included within the encounter transcript (e.g., encounter transcript 626) and/or data included within AV streams 604, 610.

The meeting (e.g., the above-described telehealth medical encounter) may include one or more of: a consultation portion; an intake portion; and a follow-up portion.

Consultation portion: An example of such a consultation portion may include but is not limited to a telehealth session in which the patient (e.g., user 538) is discussing a medical situation with the medical professional (e.g., user 542) and/or medical virtual assistant 630.

Intake Portion: An example of such an intake portion may include but is not limited to an intake session in which the patient (e.g., user 538) is initiating a telehealth medical encounter and providing information to the medical professional (e.g., user 542) and/or medical virtual assistant 630 concerning e.g., symptoms and/or issues to be discussed during the consultation portion.

Follow-Up Portion: An example of such a follow-up portion may include but is not limited to a follow-up session in which the patient (e.g., user 38) is providing follow-up information to the medical professional (e.g., user 542) and/or medical virtual assistant 630 in response to e.g., a wellness check-in call.

Participant Identification

As will be discussed below, telehealth process 510 (alone or in conjunction with ACI system 54) may identify 702 a portion of the meeting (e.g., the above-described telehealth medical encounter) associated with the patient (e.g., user 538), thus identifying a patient meeting portion (e.g., patient meeting portion 556).

Telehealth process 510 (alone or in conjunction with ACI system 54) may process 704 the meeting (e.g., the above-described telehealth medical encounter) to clarify the portion of the meeting (e.g., patient meeting portion 556) associated with the patient (e.g., user 538). For example, telehealth process 510 (alone or in conjunction with ACI system 54) may apply various noise-cancellation algorithms/processes/filters to the patient meeting portion (e.g., patient meeting portion 556) to e.g., remove background noise, eliminate crosstalk and/or reduce distortion.

When identifying 702 a portion of the meeting (e.g., the above-described telehealth medical encounter) associated with the patient (e.g., user 538), thus identifying a patient meeting portion, telehealth process 510 (alone or in conjunction with ACI system 54) may utilize 706 a voiceprint (e.g., voiceprint 558) to identify the portion of the meeting (e.g., the above-described telehealth medical encounter) associated with the patient (e.g., user 538).

As is known in the art, a voiceprint (e.g., voiceprint 558) is a digital model of the unique vocal characteristics of an individual. Voiceprints (e.g., voiceprint 558) may be created by specialized computer programs that process speech samples, wherein the creation of a voiceprint may be referred to as "enrollment" in a biometric system. A voiceprint may be created by performing "feature extraction" on one or more speech samples, wherein this feature extraction process may essentially create personalized calculations or vectors related to specific attributes that make the user's speech unique. Accordingly and if a voiceprint (e.g., voiceprint 558) had been previously created for e.g., the patient (e.g., user 538), this previously-created voiceprint (e.g., voiceprint 558) may be utilized to identify patient meeting portion 556 (i.e., the portion of the meeting associated with user 538).

Additionally/alternatively and when identifying 702 a portion of the meeting (e.g., the above-described telehealth medical encounter) associated with the patient (e.g., user 538), thus identifying a patient meeting portion, telehealth process 510 (alone or in conjunction with ACI system 54) may monitor 708 words/phrases included in the meeting (e.g., the above-described telehealth medical encounter) to identify the portion of the meeting (e.g., the above-described telehealth medical encounter) associated with the patient (e.g., user 538). Accordingly and as discussed above, telehealth process 510 (alone or in conjunction with ACI system 54) may listen for specific phases stated by the participants, such as "Hello, I am Dr. Jones . . . what brings you to the office today?" (which would indicate that the person speaking is a doctor (e.g., user 542)) or "Hello Doctor, I am having a hard time breathing for the past couple of weeks" (which would indicate that the person speaking is a patient (e.g., user 538)).

Additionally/alternatively and when identifying 702 a portion of the meeting (e.g., the above-described telehealth medical encounter) associated with the patient (e.g., user 538), thus identifying a patient meeting portion, telehealth process 510 (alone or in conjunction with ACI system 54) may monitor 710 network connections to identify the portion of the meeting (e.g., the above-described telehealth medical encounter) associated with the patient (e.g., user 538). Accordingly and as discussed above, the client electronic device (e.g., laptop computer 534) of the doctor (e.g., user 542) may access telehealth system 512 from a local IP address (e.g., 192.xxx.yyy.zzz), while the client electronic device (e.g., laptop computer 530) of the patient (e.g., user 538) may access telehealth system 512 from a remote IP address (e.g., 113.xxx.yyy.zzz).

As will be discussed below, telehealth process 510 (alone or in conjunction with ACI system 54) may identify 712 a portion of the meeting (e.g., the above-described telehealth medical encounter) associated with the medical professional (e.g., user 542), thus identifying a medical professional meeting portion (e.g., medial professional meeting portion 560).

Telehealth process 510 (alone or in conjunction with ACI system 54) may process 714 the meeting (e.g., the above-described telehealth medical encounter) to clarify the portion of the meeting (e.g., medical professional meeting portion 560) associated with the medical professional (e.g., user 542). For example, telehealth process 510 (alone or in conjunction with ACI system 54) may apply various noise-cancellation algorithms/processes/filters to the medical professional meeting portion (e.g., medical professional meeting portion 560) to e.g., remove background noise, eliminate crosstalk and/or reduce distortion.

When identifying 712 a portion of the meeting (e.g., the above-described telehealth medical encounter) associated with the medical professional (e.g., user 542), thus identifying a medical professional meeting portion, telehealth process 510 (alone or in conjunction with ACI system 54) may utilize 716 a voiceprint (e.g., voiceprint 562) to identify the portion of the meeting (e.g., the above-described telehealth medical encounter) associated with the medical professional (e.g., user 542). Accordingly and if a voiceprint (e.g., voiceprint 562) had been previously created for e.g., the medical professional (e.g., user 542), this previously-created voiceprint (e.g., voiceprint 562) may be utilized to identify medical professional meeting portion 560 (i.e., the portion of the meeting associated with user 542).

Additionally/alternatively and when identifying 712 a portion of the meeting (e.g., the above-described telehealth medical encounter) associated with the medical professional (e.g., user 542), thus identifying a medical professional meeting portion, telehealth process 510 (alone or in conjunction with ACI system 54) may monitor 718 words/phrases included in the meeting (e.g., the above-described telehealth medical encounter) to identify the portion of the meeting (e.g., the above-described telehealth medical encounter) associated with the medical professional (e.g., user 542). Accordingly and as discussed above, telehealth process 510 (alone or in conjunction with ACI system 54) may listen for specific phases stated by the participants, such as "Hello, I am Dr. Jones . . . what brings you to the office today?" (which would indicate that the person speaking is a doctor (e.g., user 542)) or "Hello Doctor, I am having a hard time breathing for the past couple of weeks" (which would indicate that the person speaking is a patient (e.g., user 538)).

Additionally/alternatively and when identifying 712 a portion of the meeting (e.g., the above-described telehealth medical encounter) associated with the medical professional (e.g., user 542), thus identifying a medical professional meeting portion, telehealth process 510 (alone or in conjunction with ACI system 54) may monitor 720 network connections to identify the portion of the meeting (e.g., the above-described telehealth medical encounter) associated with the medical professional (e.g., user 542). Accordingly and as discussed above, the client electronic device (e.g., laptop computer 534) of the doctor (e.g., user 542) may access telehealth system 512 from a local IP address (e.g., 192.xxx.yyy.zzz), while the client electronic device (e.g., laptop computer 530) of the patient (e.g., user 538) may access telehealth system 512 from a remote IP address (e.g., 113.xxx.yyy.zzz).

Medical Intelligence (Generally)
System Overview

As discussed above, meetings may occur between a patient (e.g., user 228 or user 538) and a medical entity, examples of which may include but are not limited to a medical professional (e.g., user 226 or user 542) and/or a medical virtual assistant (e.g., medical virtual assistant 238 or medical virtual assistant 630). As also discussed above, these meetings may occur as in-person medical encounters (e.g., via ambient cooperative intelligence process 10 and ACI system 54) or as telehealth medical encounters (e.g., via telehealth process 510 and telehealth system 512), wherein these meetings may include one or more of: an intake portion (which may occur prior to the consultation portion); a consultation portion (wherein the patient meets with e.g., a doctor); and/or a follow-up portion (which may occur directly or shortly after the consultation portion).

Medical intelligence process 56 may be configured to be utilized during in-person medical encounters (e.g., via ambient cooperative intelligence process 10 and ACI system 54) and/or telehealth medical encounters (e.g., via telehealth process 510 and telehealth system 512). Accordingly and while the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Informational Overlay Process:

As will be discussed below in greater detailed, medical intelligence process 56 may be configured to provide information to participants of meetings between a patient (e.g., user 228 or user 538) and a medical entity, examples of which may include but are not limited to a medical professional (e.g., user 226 or user 542), wherein this information may be provided in an unintrusive manner that does not interfere with the effectuation of the meeting.

Concept 1

As will be discussed below in greater detail, medical intelligence process 56 may be configured to render an informational window for review by a medical professional (e.g., user 542) and/or a patient (e.g., user 538) during a telehealth medical encounter (e.g., via telehealth process 510 and telehealth system 512).

Figure 11:
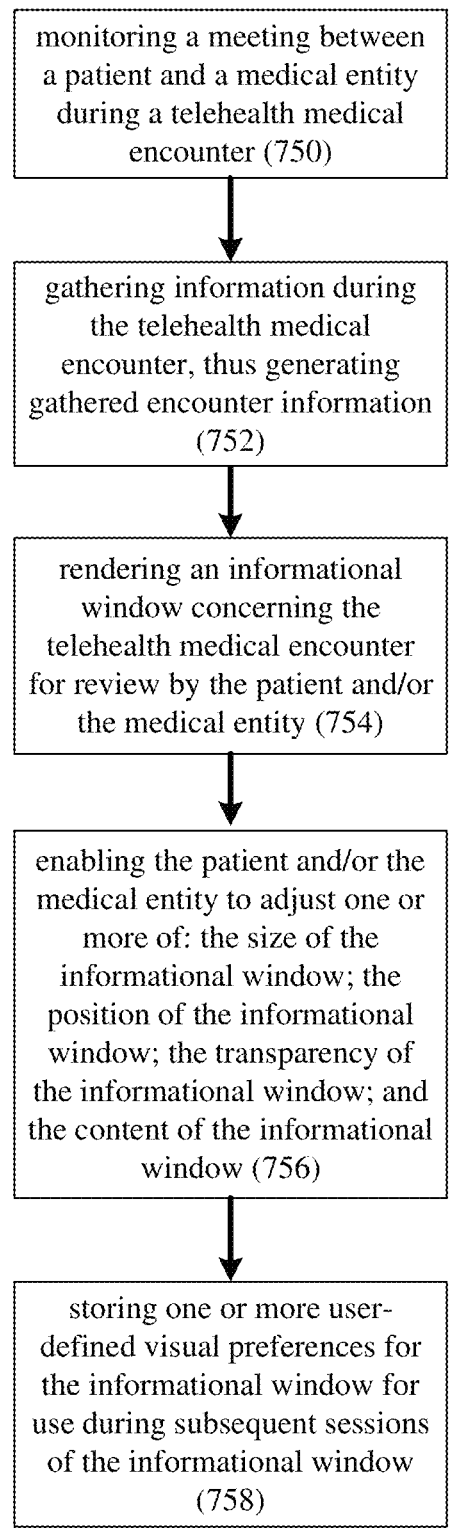
FIG. 11 is a flow chart of one implementation of the medical intelligence process of FIGS. 1 & 8.

Referring also to FIG. 11, medical intelligence process 56 may monitor 750 a meeting between a patient (e.g., user 538) and a medical entity (e.g., user 542 and/or medical virtual assistant 630) during a telehealth medical encounter (e.g., via telehealth process 510 and telehealth system 512). As discussed above, these meetings may include one or more of: an intake portion (which may occur prior to the consultation portion); a consultation portion (wherein the patient meets with e.g., a doctor); and/or a follow-up portion (which may occur directly or shortly after the consultation portion).

Accordingly and during the intake portion of the meeting, a virtual assistant (e.g., medical virtual assistant 630) may be utilized to gather intake information from the patient (e.g., user 538). Example of such intake information may include but are not limited to: name, address, phone number, emergency contact information, date of birth, height, weight, vital signs, allergies, current medications, insurance information, etc.). Further and during the consultation portion of the meeting, a medical professional (e.g., user 542) and the patient (e.g., user 538) may discuss the reason for the meeting. Additionally and during the follow-up portion of the meeting, the virtual assistant (e.g., medical virtual assistant 630) may be utilized to gather follow-up information from the patient (e.g., user 538). Example of such follow-up information may include but are not limited to: scheduling a future meeting, discussing medications and instructions, wellness check information, etc.

Medical intelligence process 56 may gather 752 information during the telehealth medical encounter, thus generating gathered encounter information (e.g., gathered encounter information 624).

Medical intelligence process 56 may render 754 an informational window (e.g., informational window 632, 634) concerning the telehealth medical encounter for review by the patient (e.g., user 538) and/or the medical entity (e.g., user 542), wherein the informational window (e.g., informational window 632, 634) may be configured to provide supplemental information (e.g., supplemental information 636, 638 respectively) based, at least in part, upon the gathered encounter information (e.g., gathered encounter information 624).

The informational window (e.g., informational window 632, 634) may be a transparent overlay informational window. For example, informational window (e.g., informational window 632, 634) may be configured to function in a similar fashion to a head-up display (i.e., positionable on top of other pieces of information without obscuring them), thus allowing the patient (e.g., user 538) and/or the medical entity (e.g., user 542) to review the supplemental information (e.g., supplemental information 636, 638 respectively) while fully participating in the telehealth medical encounter.

As is known in the art, a head-up display, also known as a HUD, is any transparent display that presents data without requiring users to look away from their usual viewpoints. The origin of the name stems from a pilot being able to view information with the head positioned "up" and looking forward, instead of angled down looking at lower instruments. A HUD also has the advantage that the pilot's eyes do not need to refocus to view the outside after looking at the optically nearer instruments.

The supplemental information (e.g., supplemental information 636, 638) provided within the informational window (e.g., informational window 632, 634) may include one of more of: patient status information; EHR-provided information; patient-provided information; patient allergy information; patient medication information; medication interaction information; and AI-generated information.

Patient Status Information: The supplemental information (e.g., supplemental information 636, 638) provided within the informational window (e.g., informational window 632, 634) may include patient status information, examples of which may include but are not limited to patient name, address, phone number, emergency contact information, date of birth, height, weight, vital signs, allergies, current medications, and insurance information. This patient status information may include current patient status information (e.g., patient status information at the time of the telehealth medical encounter) and historic patient status information (e.g., patient status information at some point prior to the telehealth medical encounter).

EHR-Provided Information: The supplemental information (e.g., supplemental information 636, 638) provided within the informational window (e.g., informational window 632, 634) may include EHR-provided information, examples of which may include but are not limited to any information that may be included within the electronic health record (EHR) of a patient (e.g., treatment history, illness history, etc.).

Patient-Provided Information: The supplemental information (e.g., supplemental information 636, 638) provided within the informational window (e.g., informational window 632, 634) may include patient-provided information, examples of which may include but are not limited to current aches, current pains, issues, and current concerns, as well as information included within the patient's health wallet (e.g., an electronic repository for the patient's health information that is controlled by the patient).

Patient Allergy Information: The supplemental information (e.g., supplemental information 636, 638) provided within the informational window (e.g., informational window 632, 634) may include patient allergy information (e.g., allergy information known by the patient that may not be included within the EHR of the patient).

Patient Medication Information: The supplemental information (e.g., supplemental information 636, 638) provided within the informational window (e.g., informational window 632, 634) may include patient medication information (e.g., medication information known by the patient that may not be included within the EHR of the patient).

Medication Interaction Information: The supplemental information (e.g., supplemental information 636, 638) provided within the informational window (e.g., informational window 632, 634) may include medication interaction information, examples of which may include but are not limited to known side effects/interactions of medication currently being taken by the patient and known side effects/interactions of medication being considered for the patient.

AI-Generated Information: The supplemental information (e.g., supplemental information 636, 638) provided within the informational window (e.g., informational window 632, 634) may include AI-generated information.

A will be discussed below in greater detail, this AI-Generated Information may include one or more of: AI-generated best practices information; AI-generated medical encounter workflow information; AI-generated recommendations; AI-generated suggested inquiry information; and AI-generated observational information (each of which will be discussed below in greater detail).

AI-Generated Best Practices Information: The AI-Generated Best Practices Information may include information intended to define or provide guidance concerning one or more proposed best practices concerning e.g., the telehealth medical encounter.

AI-Generated Medical Encounter Workflow Information: The AI-Generated Medical Encounter Workflow Information may include information intended to define or provide guidance concerning one or more proposed workflows concerning e.g., the telehealth medical encounter.

AI-Generated Recommendations: The AI-Generated Recommendations may include information intended to define or provide guidance concerning one or more proposed recommendations concerning e.g., the telehealth medical encounter.

AI-Generated Suggested Inquiry Information: The AI-Generated Suggested Inquiry Information may include information intended to define or provide guidance concerning one or more proposed inquiries concerning e.g., the telehealth medical encounter.

AI-Generated Observational Information: The AI-Generated Observational Information may include information intended to provide observations concerning e.g., the telehealth medical encounter. As will be discussed below in greater detail, this AI-Generated Observational Information may include one or more of: AI-generated audible observational information (e.g., observational information defined within audio-based content associated with e.g., the telehealth medical encounter), and AI-generated visual observational information (e.g., observational information defined within image-based content and/or video-based content associated with e.g., the telehealth medical encounter).

Medical intelligence process 56 may enable 756 the patient (e.g., user 538) and/or the medical entity (e.g., user 542) to adjust one or more of: the size of the informational window (e.g., informational window 632, 634); the position of the informational window (e.g., informational window 632, 634); the transparency of the informational window (e.g., informational window 632, 634); and the content of the informational window (e.g., informational window 632, 634).

Further, medical intelligence process 56 may store 758 one or more user-defined visual preferences (e.g., user preferences 640) for the informational window (e.g., informational window 632, 634) for use during subsequent sessions of the informational window (e.g., informational window 632, 634).

Intelligent Monitoring and Guidance (Generally):

As will be discussed below in greater detailed, medical intelligence process 56 may be configured to monitor meetings between a patient (e.g., user 228 or user 538) and a medical entity, examples of which may include but are not limited to a medical professional (e.g., user 226 or user 542) and/or a medical virtual assistant (e.g., medical virtual assistant 238 or medical virtual assistant 630). These meetings may occur as in-person medical encounters (e.g., via ambient cooperative intelligence process 10 and ACI system 54) or as telehealth medical encounters (e.g., via telehealth process 510 and telehealth system 512). As will be discussed below in greater detail, medical intelligence process 56 may then provide guidance (e.g., in the form of supplemental information) to the medical professional (e.g., user 226 or user 542) with respect to the same.

Concept 2

As will be discussed below in greater detail, medical intelligence process 56 may be configured to provide medical encounter workflow information for review by a medical professional (e.g., user 226 or user 542) during in-person medical encounters (e.g., via ambient cooperative intelligence process 10 and ACI system 54) and/or telehealth medical encounters (e.g., via telehealth process 510 and telehealth system 512). While the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Figure 12:
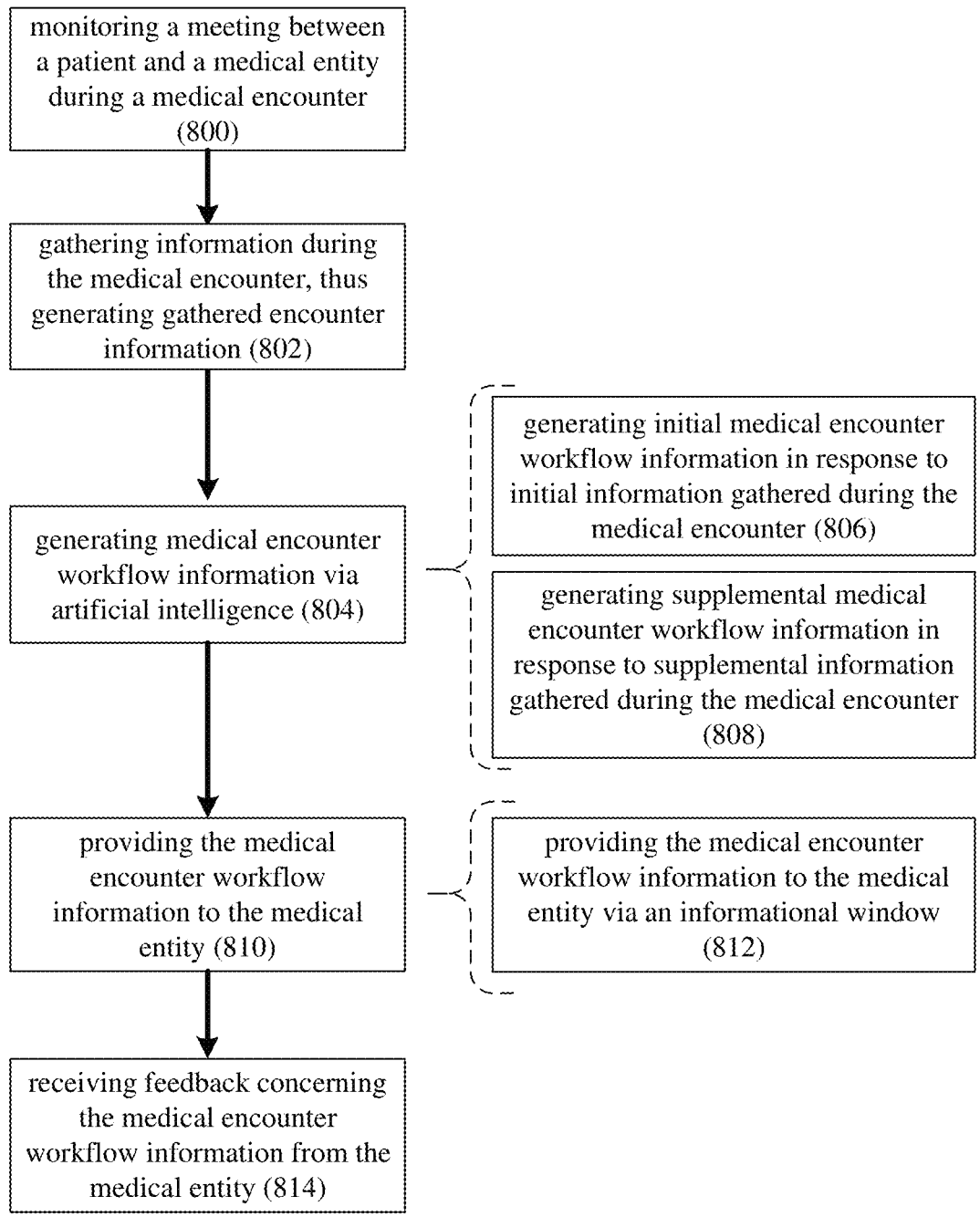
FIG. 12 is a flow chart of another implementation of the medical intelligence process of FIGS. 1 & 8.

Referring also to FIG. 12, medical intelligence process 56 may monitor 800 a meeting between a patient (e.g., user 538) and a medical entity (e.g., user 542 and/or medical virtual assistant 630) during a medical encounter (e.g., a telehealth medical encounter).

Medical intelligence process 56 may gather 802 information during the medical encounter (e.g., a telehealth medical encounter), thus generating gathered encounter information (e.g., gathered encounter information 624).

Medical intelligence process 56 may generate 804 medical encounter workflow information (e.g., medical encounter workflow information 642) via artificial intelligence, wherein the medical encounter workflow information (e.g., medical encounter workflow information 642) may be based at least in part upon the gathered encounter information (e.g., gathered encounter information 624) and may be configured to provide guidance to the medical entity (e.g., user 542) concerning a desired workflow for the medical encounter (e.g., a telehealth medical encounter), wherein such a desired workflow may quantify a preferred manner in which the medical encounter (e.g., a telehealth medical encounter) should proceed.

The medical encounter workflow information (e.g., medical encounter workflow information 642) may be based upon one or more best practices (e.g., best practices 644), wherein these one or more best practices (e.g., best practices 644) may be definable by one or more medical organizations/institutions (e.g., organizations/institutions 646). Examples of such medical organizations/institutions (e.g., organizations/institutions 646) may include but are not limited to the hospital network for which user 542 works, the insurance company through which user 538 is insured, local/state/regional licensing boards, etc.

When generating 804 medical encounter workflow information (e.g., medical encounter workflow information 642) via artificial intelligence, medical intelligence process 56 may:

generate 806 initial medical encounter workflow information (e.g., an initial version of medical encounter workflow information 642) in response to initial information gathered during the medical encounter (e.g., a telehealth medical encounter); and generate 808 supplemental medical encounter workflow information (e.g., a supplemental version of medical encounter workflow information 642) in response to supplemental information gathered during the medical encounter (e.g., a telehealth medical encounter).

Specifically, when medical intelligence process 56 has more knowledge as to what the medical encounter (e.g., a telehealth medical encounter) is about, the workflow may be more defined. However, up until that point, the workflow may be more fluid/wandering. For example, if the patient (e.g., user 538) is initially explaining to the medical entity (e.g., user 542) that they are having difficulty breathing, medical intelligence process 56 may initiate a first workflow to investigate whether the patient (e.g., user 538) has COVID, notifying the medical entity (e.g., user 542) that "This Patient may have COVID" and prompting them to make inquiries about sense of taste and smell. In the event that it seems that the patient (e.g., user 538) does not have COVID, medical intelligence process 56 may initiate a second workflow to investigate whether the patient (e.g., user 538) has pneumonia.

Medical intelligence process 56 may provide 810 the medical encounter workflow information (e.g., medical encounter workflow information 642) to the medical entity (e.g., user 542). When providing 810 the medical encounter workflow information (e.g., medical encounter workflow information 642) to the medical entity (e.g., user 542), medical intelligence process 56 may provide 812 the medical encounter workflow information (e.g., medical encounter workflow information 642) to the medical entity (e.g., user 542) via an informational window (e.g., informational window 634).

The informational window (e.g., informational window 634) may be a transparent overlay informational window. As discussed above, the informational window (e.g., informational window 634) may be configured to function in a similar fashion to a head-up display (i.e., positionable on top of other pieces of information without obscuring them), thus allowing the medical entity (e.g., user 542) to review the medical encounter workflow information (e.g., medical encounter workflow information 642) while fully participating in the telehealth medical encounter.

Generally speaking, medical intelligence process 56 may observe the progression of the medical encounter (e.g., a telehealth medical encounter) and may direct the medical encounter (e.g., a telehealth medical encounter) via prompts (e.g., within informational window 634) along a desired workflow that may be based upon one or more best practices (e.g., best practices 644), wherein these best practices (e.g., best practices 644) may be definable by organizations/institutions 646. For example, when proscribing medication, medical intelligence process 56 may confirm that the medical entity (e.g., user 542) inquiries about medicine allergies, and prior allergic reactions. In the event that the medical entity (e.g., user 542) does not make such inquiries, medical intelligence process 56 may prompt (e.g., within informational window 634) the medical entity (e.g., user 542) to do so. Further, medical intelligence process 56 may confirm that standard closing questions are used prior to ending the medical encounter (e.g., a telehealth medical encounter). For example, if the medical entity (e.g., user 542) does not inquire if the patient (e.g., user 538) has any questions before ending the medical encounter (e.g., a telehealth medical encounter), medical intelligence process 56 may prompt (e.g., within informational window 634) the medical entity (e.g., user 542) to do so.

Medical intelligence process 56 may receive 814 feedback concerning the medical encounter workflow information (e.g., medical encounter workflow information 642) from the medical entity (e.g., user 542). This feedback may be active, wherein medical intelligence process 56 may inquire as to whether the medical encounter workflow information was helpful. Additionally/alternatively, this feedback may be passive, wherein medical intelligence process 56 may gauge the quality of the medical encounter workflow information by monitoring whether the medical entity (e.g., user 542) follows the prompts of medical intelligence process 56.

Concept 3

As will be discussed below in greater detail, medical intelligence process 56 may be configured to process image-based content and provide guidance for review by a medical professional (e.g., user 226 or user 542) during in-person medical encounters (e.g., via ambient cooperative intelligence process 10 and ACI system 54) and/or telehealth medical encounters (e.g., via telehealth process 510 and telehealth system 512). While the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Figure 13:
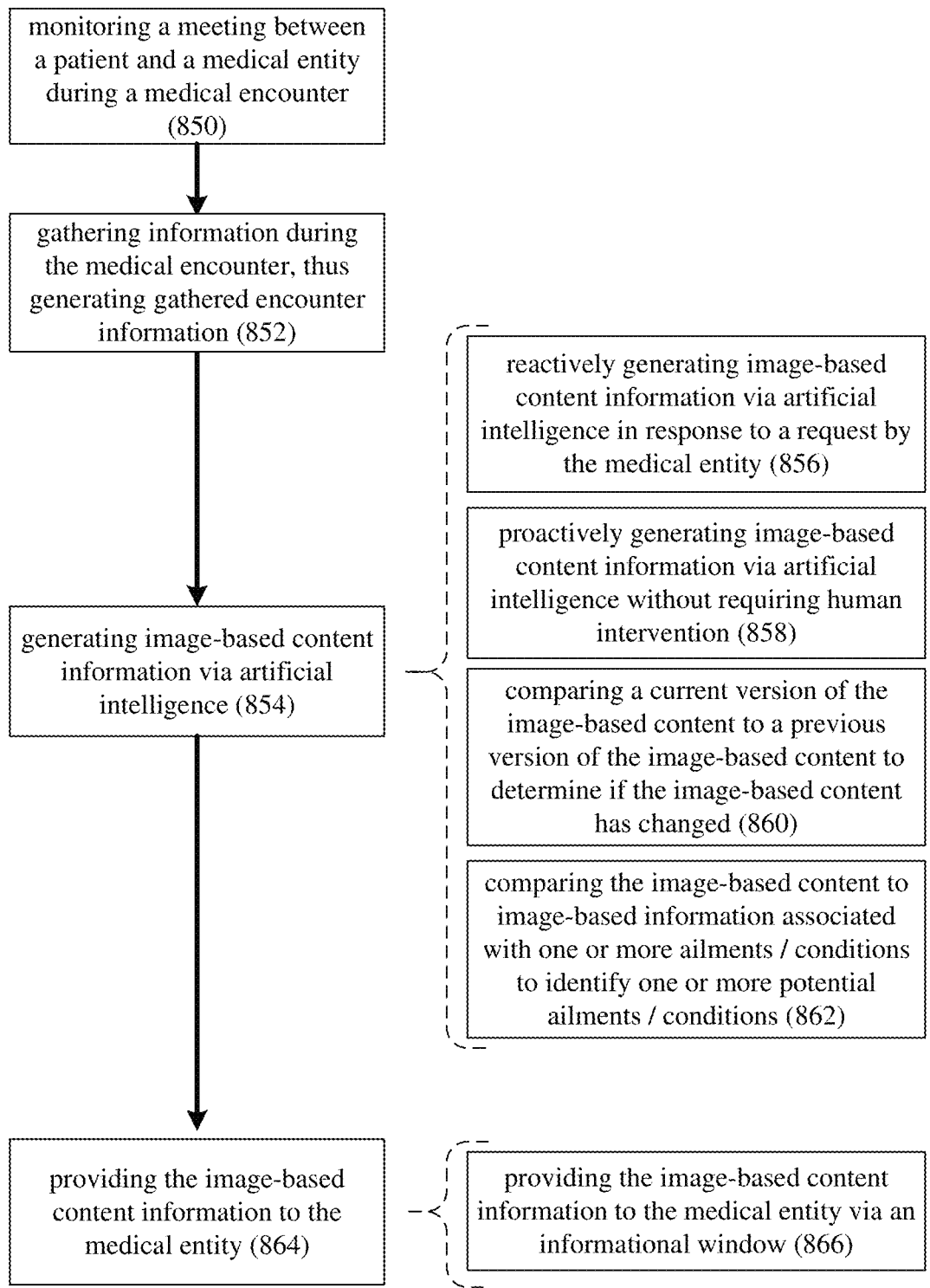
FIG. 13 is a flow chart of another implementation of the medical intelligence process of FIGS. 1 & 8.

Referring also to FIG. 13, medical intelligence process 56 may monitor 850 a meeting between a patient (e.g., user 538) and a medical entity (e.g., user 542 and/or medical virtual assistant 630) during a medical encounter (e.g., a telehealth medical encounter).

Medical intelligence process 56 may gather 852 information during the medical encounter (e.g., a telehealth medical encounter), thus generating gathered encounter information (e.g., gathered encounter information 624). This gathered encounter information (e.g., gathered encounter information 624) may include image-based content (e.g., image-based content 648) of the patient (e.g., user 538). An example of image-based content 648 may include but is not limited to a still image/photograph/screen capture of e.g., a wound, a bruise or a mole on the patient (e.g., user 538).

Medical intelligence process 56 may generate 854 image-based content information (e.g., image-based content information 650) via artificial intelligence, wherein the image-based content information (e.g., image-based content information 650) may be based at least in part upon the image-based content (e.g., image-based content 648) and/or the gathered encounter information (e.g., gathered encounter information 624) and may be configured to provide guidance to the medical entity (e.g., user 542) concerning the image-based content (e.g., image-based content 648). For example, medical intelligence process 56 may capture image-based content 648 (e.g., the still image, the photograph, the screen capture) of e.g., the wound/bruise/mole on the patient (e.g., user 538).

When generating 854 image-based content information (e.g., image-based content information 650) via artificial intelligence, medical intelligence process 56 may reactively generate 856 image-based content information (e.g., image-based content information 650) via artificial intelligence in response to a request by the medical entity (e.g., user 542). For example, assume that the patient (e.g., user 538) has a mole on their forehead that is visible by medical entity (e.g., user 542) during the medical encounter (e.g., a telehealth medical encounter). Accordingly, the medical entity (e.g., user 542) may reactively generate 856 the image-based content information (e.g., image-based content information 650) by manually initiating the capture of image-based content 648 (e.g., the still image, the photograph, the screen capture) of the mole on the patient (e.g., user 538).

Additionally/alternatively and when generating 854 image-based content information (e.g., image-based content information 650) via artificial intelligence, medical intelligence process 56 may proactively generate 858 image-based content information (e.g., image-based content information 850) via artificial intelligence without requiring human intervention. For example and continuing with the example in which the patient (e.g., user 538) has a mole on their forehead that is visible during the medical encounter (e.g., a telehealth medical encounter), medical intelligence process 56 may proactively generate 858 image-based content information (e.g., image-based content information 850) via artificial intelligence without requiring human intervention (e.g., without requiring initiation by the medical entity (e.g., user 542).

Additionally/alternatively and when generating 854 image-based content information (e.g., image-based content information 650) via artificial intelligence, medical intelligence process 56 may compare 860 a current version of the image-based content (e.g., image-based content 648) to a previous version of the image-based content (e.g., image-based content 648) to determine if the image-based content (e.g., image-based content 648) has changed. Continuing with the example in which the patient (e.g., user 538) has a mole on their forehead that is visible during the medical encounter (e.g., a telehealth medical encounter), medical intelligence process 56 may repeatedly capture image-based content 648 (e.g., the still image, the photograph, the screen capture) of the mole on the patient (e.g., user 538) during every medical encounter (e.g., once every six months during scheduled telehealth medical encounters), thus creating a temporally spaced sequence of image-based content 648. Medical intelligence process 56 may compare 860 a current version (e.g., the latest version) of the image-based content (e.g., image-based content 648) to a previous version of the image-based content (e.g., image-based content 648) to determine if the image-based content (e.g., image-based content 648) has changed (which may be indicative of a cancerous condition).

Additionally/alternatively and when generating 854 image-based content information (e.g., image-based content information 650) via artificial intelligence, medical intelligence process 56 may compare 862 the image-based content (e.g., image-based content 648) to image-based information (e.g., image-based information 652) associated with one or more ailments/conditions to identify one or more potential ailments/conditions. For example and continuing with the example in which the patient (e.g., user 538) has a mole on their forehead that is visible during the medical encounter (e.g., a telehealth medical encounter), medical intelligence process 56 may capture image-based content 648 (e.g., the still image, the photograph, the screen capture) of the mole on the patient (e.g., user 538) and may compare 862 the image-based content (e.g., image-based content 648) to image-based information (e.g., image-based information 652) associated with one or more ailments/conditions (e.g., pictures of cancerous moles) to identify one or more potential ailments/conditions (e.g., one or more skin cancers).

Generally speaking, medical intelligence process 56 may enable the capturing of close proximity/high resolution images (e.g., image-based content 648) that may be incorporated into a medical record, wherein these close proximity/high resolution images (e.g., image-based content 648) may be processed by medical intelligence process 56 to assess any visual concerns (e.g., to gauge wound healing, paleness, bruising, jaundice, etc.).

Medical intelligence process 56 may provide 864 the image-based content information (e.g., image-based content information 650) to the medical entity (e.g., user 542). When providing 864 the image-based content information (e.g., image-based content information 650) to the medical entity (e.g., user 542), medical intelligence process 56 may provide 866 the image-based content information (e.g., image-based content information 650) to the medical entity (e.g., user 542) via an informational window (e.g., informational window 634). Accordingly and continuing with the above-stated example, informational window 634 may display image-based content information 650 that says "This Patient shows signs of skin cancer"

The informational window (e.g., informational window 634) may be a transparent overlay informational window. As discussed above, the informational window (e.g., informational window 634) may be configured to function in a similar fashion to a head-up display (i.e., positionable on top of other pieces of information without obscuring them), thus allowing the medical entity (e.g., user 542) to review the image-based content information (e.g., image-based content information 650) while fully participating in the telehealth medical encounter.

Medical intelligence process 56 may seek approval from the patient (e.g., user 538) before image-based content 648 (e.g., the still image, the photograph, the screen capture) is captured and/or added to the medical record (e.g., medical record 628) of the patient (e.g., user 538)

Concept 4

As will be discussed below in greater detail, medical intelligence process 56 may be configured to process audio-based content and provide guidance for review by a medical professional (e.g., user 226 or user 542) during in-person medical encounters (e.g., via ambient cooperative intelligence process 10 and ACI system 54) and/or telehealth medical encounters (e.g., via telehealth process 510 and telehealth system 512). While the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Figure 14:
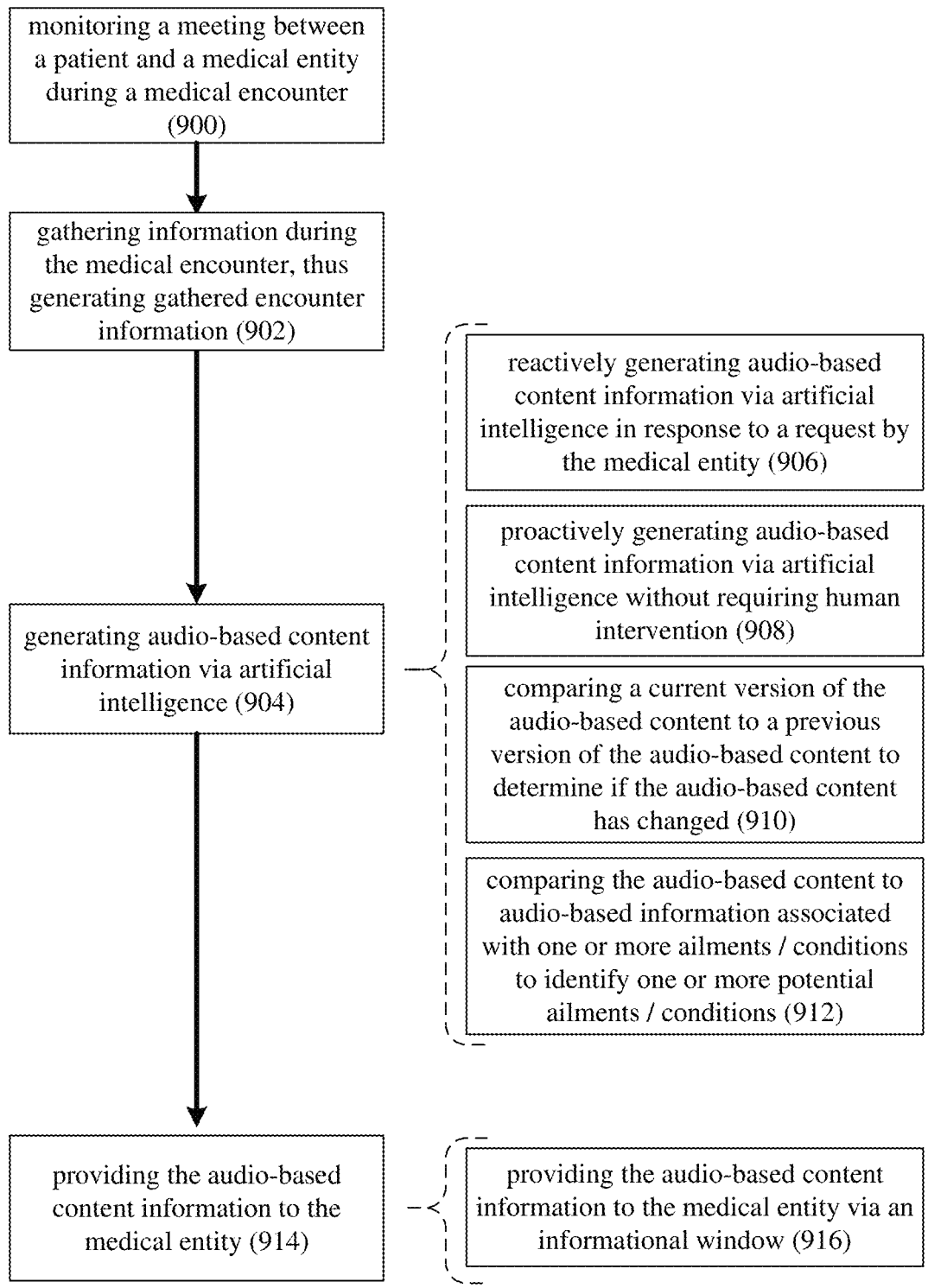
FIG. 14 is a flow chart of another implementation of the medical intelligence process of FIGS. 1 & 8.

Referring also to FIG. 14, medical intelligence process 56 may monitor 900 a meeting between a patient (e.g., user 538) and a medical entity (e.g., user 542 and/or medical virtual assistant 630) during a medical encounter (e.g., a telehealth medical encounter).

Medical intelligence process 56 may gather 902 information during the medical encounter (e.g., a telehealth medical encounter), thus generating gathered encounter information (e.g., gathered encounter information 624). This gathered encounter information (e.g., gathered encounter information 624) may include audio-based content (e.g., audio-based content 654) of the patient (e.g., user 538). An example of audio-based content 654 may include but is not limited to an audio recording of the voice of the patient (e.g., user 538).

Medical intelligence process 56 may generate 904 audio-based content information (e.g., audio-based content information 656) via artificial intelligence, wherein the audio-based content information (e.g., audio-based content information 656) may be based at least in part upon the audio-based content (e.g., audio-based content 654) and/or the gathered encounter information (e.g., gathered encounter information 624) and may be configured to provide guidance to the medical entity (e.g., user 542) concerning the audio-based content (e.g., audio-based content 654). For example, medical intelligence process 56 may capture audio-based content 654 (e.g., an audio recording of a conversation between the patient (e.g., user 538) and the medical entity (e.g., user 542).

When generating 904 audio-based content information (e.g., audio-based content information 656) via artificial intelligence, medical intelligence process 56 may reactively generate 906 audio-based content information (e.g., audio-based content information 656) via artificial intelligence in response to a request by the medical entity (e.g., user 542). For example, assume that the patient (e.g., user 538) is slurring their speech during the medical encounter (e.g., a telehealth medical encounter). Accordingly, the medical entity (e.g., user 542) may reactively generate 906 the audio-based content information (e.g., audio-based content information 656) by manually initiating the recording of audio-based content 654 (e.g., the audio recording of the speech) of the patient (e.g., user 538).

Additionally/alternatively and when generating 904 audio-based content information (e.g., audio-based content information 656) via artificial intelligence, medical intelligence process 56 may proactively generate 908 audio-based content information (e.g., audio-based content information 656) via artificial intelligence without requiring human intervention. Continuing with the example in which the patient (e.g., user 538) is slurring their speech during the medical encounter (e.g., a telehealth medical encounter), medical intelligence process 56 may proactively generate 908 audio-based content information (e.g., audio-based content information 656) via artificial intelligence without requiring human intervention (e.g., without requiring initiation by the medical entity (e.g., user 542).

Additionally/alternatively and when generating 904 audio-based content information (e.g., audio-based content information 656) via artificial intelligence, medical intelligence process 56 may compare 910 a current version of the audio-based content (e.g., audio-based content 654) to a previous version of the audio-based content (e.g., audio-based content 654) to determine if the audio-based content (e.g., audio-based content 654) has changed. Continuing with the example in which the patient (e.g., user 538) is slurring their speech during the medical encounter (e.g., a telehealth medical encounter), medical intelligence process 56 may repeatedly capture audio-based content 654 (e.g., the audio recording of the speech) of the patient (e.g., user 538)

during every medical encounter (e.g., once every six months during scheduled telehealth medical encounters), thus creating a temporally spaced sequence of audio-based content 654. Medical intelligence process 56 may compare 910 a current version (e.g., the latest version) of the audio-based content (e.g., audio-based content 654) to a previous version of the audio-based content (e.g., audio-based content 654) to determine if the audio-based content (e.g., audio-based content 654) has changed (which may be indicative of a degenerating neurological condition).

Additionally/alternatively and when generating 904 audio-based content information (e.g., audio-based content information 656) via artificial intelligence, medical intelligence process 56 may compare 912 the audio-based content (e.g., audio-based content 654) to audio-based information (e.g., audio-based information 658) associated with one or more ailments/conditions to identify one or more potential ailments/conditions. Continuing with the example in which the patient (e.g., user 538) is slurring their speech during the medical encounter (e.g., a telehealth medical encounter), medical intelligence process 56 may capture audio-based content 654 (e.g., the audio recording of the speech) of the patient (e.g., user 538) and may compare 912 the audio-based content (e.g., audio-based content 654) to audio-based information (e.g., audio-based information 658) associated with one or more ailments/conditions (e.g., audio recordings of people who had strokes) to identify one or more potential ailments/conditions (e.g., strokes, brain bleeds, etc.).

Generally speaking, medical intelligence process 56 may process the audio of the medical encounter (e.g., a telehealth medical encounter) to determine if the patient (e.g., user 538) is afflicted with a disease (e.g., depression, dementia, vocal cord problems, respiratory ailments).

Medical intelligence process 56 may provide 914 the audio-based content information (e.g., audio-based content information 656) to the medical entity (e.g., user 542). When providing 914 the audio-based content information (e.g., audio-based content information 656) to the medical entity (e.g., user 542), medical intelligence process 56 may provide 916 the audio-based content information (e.g., audio-based content information 656) to the medical entity (e.g., user 542) via an informational window (e.g., informational window 634). Accordingly and continuing with the above-stated example, informational window 634 may display audio-based content information 656 that says "This Patient shows signs of a stroke/brain bleed".

The informational window (e.g., informational window 634) may be a transparent overlay informational window. As discussed above, the informational window (e.g., informational window 634) may be configured to function in a similar fashion to a head-up display (i.e., positionable on top of other pieces of information without obscuring them), thus allowing the medical entity (e.g., user 542) to review the audio-based content information (e.g., audio-based content information 656) while fully participating in the telehealth medical encounter.

Medical intelligence process 56 may seek approval from the patient (e.g., user 538) before audio-based content (e.g., audio-based content 654) is recorded and/or added to the medical record (e.g., medical record 628) of the patient (e.g., user 538).

Concept 5

As will be discussed below in greater detail, medical intelligence process 56 may be configured to process video-based content and provide guidance for review by a medical professional (e.g., user 226 or user 542) during in-person medical encounters (e.g., via ambient cooperative intelligence process 10 and ACI system 54) and/or telehealth medical encounters (e.g., via telehealth process 510 and telehealth system 512). While the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Figure 15:
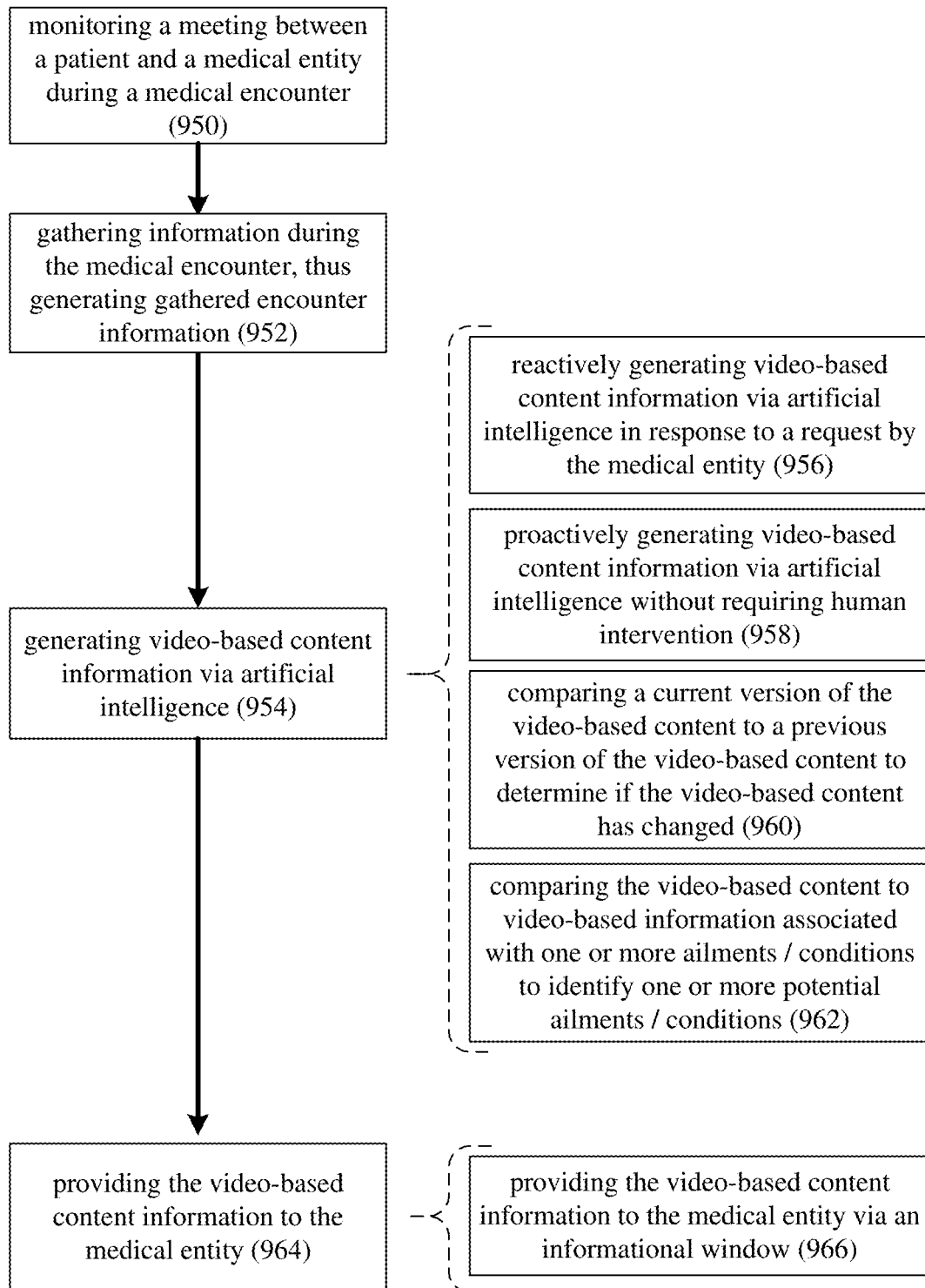
FIG. 15 is a flow chart of another implementation of the medical intelligence process of FIGS. 1 & 8.

Referring also to FIG. 15, medical intelligence process 56 may monitor 950 a meeting between a patient (e.g., user 538) and a medical entity (e.g., user 542 and/or medical virtual assistant 630) during a medical encounter (e.g., a telehealth medical encounter).

Medical intelligence process 56 may gather 952 information during the medical encounter (e.g., a telehealth medical encounter), thus generating gathered encounter information (e.g., gathered encounter information 624). This gathered encounter information (e.g., gathered encounter information 624) may include video-based content (e.g., video-based content 660) of the patient (e.g., user 538). An example of video-based content 660 may include but is not limited to a video recording of the patient (e.g., user 538).

Medical intelligence process 56 may generate 954 video-based content information (e.g., video-based content information 662) via artificial intelligence, wherein the video-based content information (e.g., video-based content information 662) may be based at least in part upon the video-based content (e.g., video-based content 660) and/or the gathered encounter information (e.g., gathered encounter information 624) and may be configured to provide guidance to the medical entity (e.g., user 542) concerning the video-based content (e.g., video-based content 662). For example, medical intelligence process 56 may capture video-based content 660 (e.g., a video recording of a meeting between the patient (e.g., user 538) and the medical entity (e.g., user 542).

When generating 954 video-based content information (e.g., video-based content information 662) via artificial intelligence, medical intelligence process 56 may reactively generate 956 video-based content information (e.g., video-based content information 662) via artificial intelligence in response to a request by the medical entity (e.g., user 542). For example, assume that the patient (e.g., user 538) is experiencing hand tremors during the medical encounter (e.g., a telehealth medical encounter). Accordingly, the medical entity (e.g., user 542) may reactively generate 956 the video-based content information (e.g., video-based content information 662) by manually initiating the recording of video-based content 660 (e.g., the video recording of the hand tremors) of the patient (e.g., user 538).

When generating 954 video-based content information (e.g., video-based content information 662) via artificial intelligence, medical intelligence process 56 may proactively generate 958 video-based content information (e.g., video-based content information 662) via artificial intelligence without requiring human intervention. Continuing with the example in which the patient (e.g., user 538) is experiencing hand tremors during the medical encounter (e.g., a telehealth medical encounter), medical intelligence process 56 may proactively generate 958 video-based content information (e.g., video-based content information 662) via artificial intelligence without requiring human intervention (e.g., without requiring initiation by the medical entity (e.g., user 542).

When generating 954 video-based content information (e.g., video-based content information 662) via artificial intelligence, medical intelligence process 56 may compare 960 a current version of the video-based content (e.g., video-based content 660) to a previous version of the video-based content (e.g., video-based content 660) to determine if the video-based content (e.g., video-based content 660) has changed. Continuing with the example in which the patient (e.g., user 538) is experiencing hand tremors during the medical encounter (e.g., a telehealth medical encounter), medical intelligence process 56 may repeatedly capture video-based content 660 (e.g., the video recording of the hand tremors) of the patient (e.g., user 538) during every medical encounter (e.g., once every six months during scheduled telehealth medical encounters), thus creating a temporally spaced sequence of video-based content 660. Medical intelligence process 56 may compare 960 a current version (e.g., the latest version) of the video-based content (e.g., video-based content 660) to a previous version of the video-based content (e.g., video-based content 660) to determine if the video-based content (e.g., video-based content 660) has changed (which may be indicative of e.g., advancing Parkinson's disease).

When generating 954 video-based content information (e.g., video-based content information 662) via artificial intelligence, medical intelligence process 56 may compare 962 the video-based content (e.g., video-based content 660) to video-based information (e.g., video-based information 664) associated with one or more ailments/conditions to identify one or more potential ailments/conditions. Continuing with the example in which the patient (e.g., user 538) is experiencing hand tremors during the medical encounter (e.g., a telehealth medical encounter), medical intelligence process 56 may capture video-based content 660 (e.g., the video recording of the hand tremors) of the patient (e.g., user 538) and may compare 962 the video-based content (e.g., video-based content 660) to video-based information (e.g., video-based information 664) associated with one or more ailments/conditions (e.g., video recordings of people who had Parkinson's disease) to identify one or more potential ailments/conditions (e.g., Parkinson's disease).

Generally speaking, medical intelligence process 56 may process the video of the medical encounter (e.g., a telehealth medical encounter) to determine if the patient (e.g., user 538) is afflicted with a disease (e.g., depression, dementia, Alzheimer's, Parkinson's, hypertension (via skin pulsations), elevated heart rate (via skin pulsations), respiratory ailments, mobility problems, signs of spousal abuse, signs of child abuse, etc.

Medical intelligence process 56 may provide 964 the video-based content information (e.g., video-based content information 662) to the medical entity (e.g., user 542). When providing 964 the video-based content information (e.g., video-based content information 662) to the medical entity (e.g., user 542), medical intelligence process 56 may provide 966 the video-based content information (e.g., video-based content information 662) to the medical entity (e.g., user 542) via an informational window (e.g., informational window 634). Accordingly and continuing with the above-stated example, informational window 634 may display video-based content information 662 that says "This Patient shows signs of Parkinson's Disease".

The informational window (e.g., informational window 634) may be a transparent overlay informational window. As discussed above, the informational window (e.g., informational window 634) may be configured to function in a similar fashion to a head-up display (i.e., positionable on top of other pieces of information without obscuring them), thus allowing the medical entity (e.g., user 542) to review the video-based content information (e.g., audio-based content information 662) while fully participating in the telehealth medical encounter.

Medical intelligence process 56 may seek approval from the patient (e.g., user 538) before video-based content (e.g., video-based content 660) is recorded and/or added to the medical record (e.g., medical record 628) of the patient (e.g., user 538).

Concept 6

As will be discussed below in greater detail, medical intelligence process 56 may be configured to provide guidance concerning third-party encounters for review by a medical professional (e.g., user 226 or user 542) during in-person medical encounters (e.g., via ambient cooperative intelligence process 10 and ACI system 54) and/or telehealth medical encounters (e.g., via telehealth process 510 and telehealth system 512). While the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Figure 16:
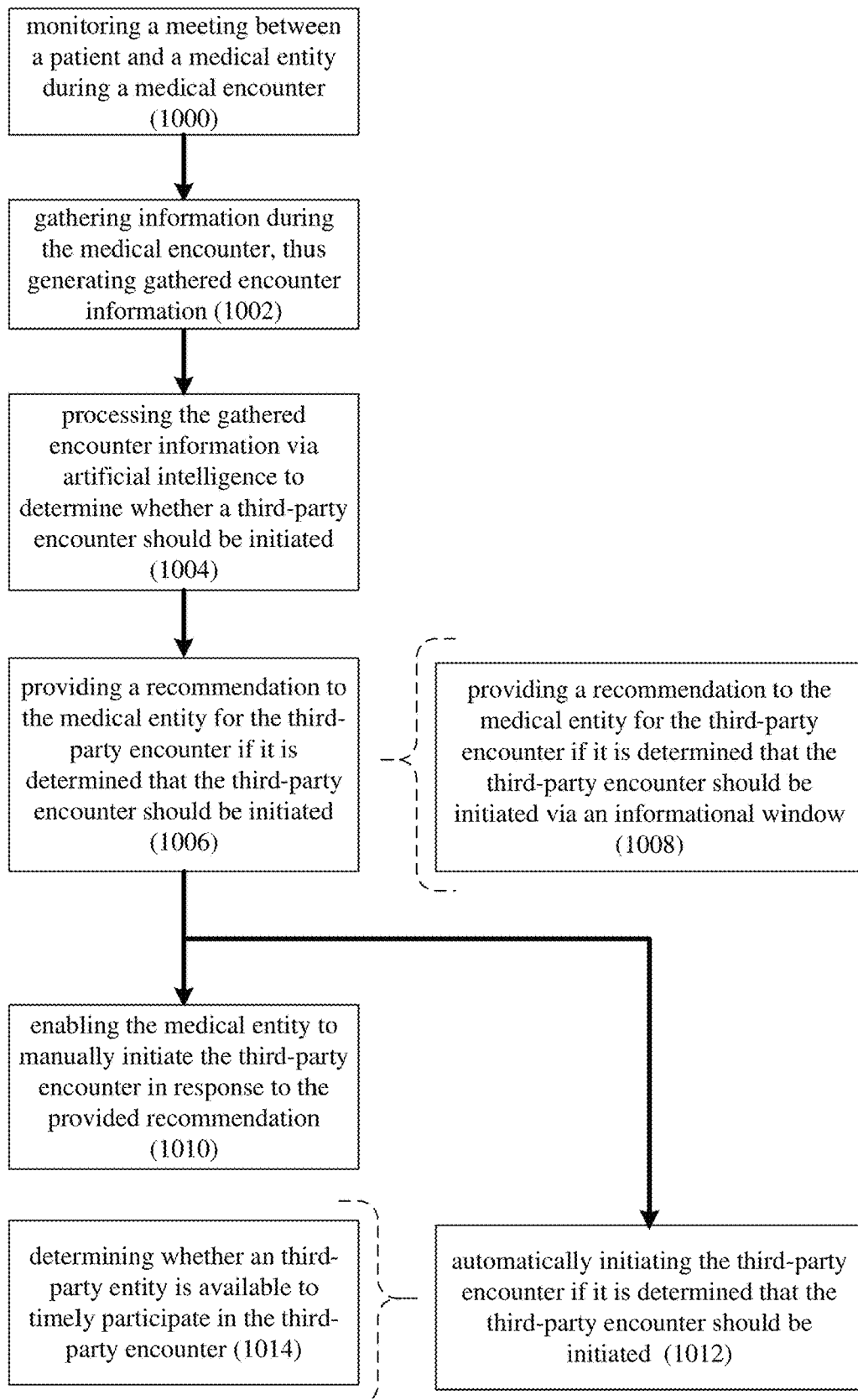
FIG. 16 is a flow chart of another implementation of the medical intelligence process of FIGS. 1 & 8.

Referring also to FIG. 16, medical intelligence process 56 may monitor 1000 a meeting between a patient (e.g., user 538) and a medical entity (e.g., user 542 and/or medical virtual assistant 630) during a medical encounter (e.g., a telehealth medical encounter).

Medical intelligence process 56 may gather 1002 information during the medical encounter (e.g., a telehealth medical encounter), thus generating gathered encounter information (e.g., gathered encounter information 624).

Medical intelligence process 56 may process 1004 the gathered encounter information (e.g., gathered encounter information 624) via artificial intelligence to determine whether a third-party encounter should be initiated. If it is determined that the third-party encounter should be initiated, medical intelligence process 56 may provide 1006 a recommendation (e.g., recommendation 666) to the medical entity (e.g., user 542) for the third-party encounter. Additionally, one or more third-party providers available for the third-party encounter may be identified. Further, the medical entity may be enabled to specify a particular third-party provider.

When providing 1006 a recommendation (e.g., recommendation 666) to the medical entity (e.g., user 542) for the third-party encounter if it is determined that the third-party encounter should be initiated, medical intelligence process 56 may provide 1008 a recommendation (e.g., recommendation 666) to the medical entity (e.g., user 542) for the third-party encounter via an informational window (e.g., informational window 634) if it is determined that the third-party encounter should be initiated.

The informational window (e.g., informational window 634) may be a transparent overlay informational window. As discussed above, the informational window (e.g., informational window 634) may be configured to function in a similar fashion to a head-up display (i.e., positionable on top of other pieces of information without obscuring them), thus allowing the medical entity (e.g., user 542) to review the recommendation (e.g., recommendation 666) while fully participating in the telehealth medical encounter Continuing with the example in which the patient (e.g., user 538) has a mole on their forehead that is visible during the medical encounter (e.g., a telehealth medical encounter), medical intelligence process 56 may process 1004 the gathered encounter information (e.g., gathered encounter information 624) via artificial intelligence to determine whether a third-party encounter should be initiated. Assume that medical intelligence process 56 determines that it is probable that the patient (e.g., user 538) has skin cancer. Accordingly, medical intelligence process 56 may provide 1006 a recommendation (e.g., recommendation 666) to the medical entity (e.g., user 542) for a third-party encounter with e.g., a dermatologist and/or an oncologist.

Medical intelligence process 56 may enable 1010 the medical entity (e.g., user 542) to manually initiate the third-party encounter in response to the provided recommendation (e.g., recommendation 666). For example and assuming that the medical entity (e.g., user 542) agrees with the recommendation (e.g., recommendation 666) provided, the medical entity (e.g., user 542) may manually initiate the third-party encounter with third-party entity 668 (e.g., a dermatologist and/or an oncologist) in response to the recommendation (e.g., recommendation 666). Additionally/alternatively, medical intelligence process 56 may identify one or more third-party providers that are available for the third-party encounter. For example, medical intelligence process 56 may present the medical entity (e.g., user 542) with a list (not shown) of available third-party entities (e.g., dermatologists and/or oncologists) from which the medical entity (e.g., user 542) may make a selection. Additionally,/alternatively, the medical entity (e.g., user 542) may be enabled to specify a particular third-party provider (e.g., from the list of available third-party entities (not shown))

Additionally/alternatively, medical intelligence process 56 may automatically initiate 1012 the third-party encounter if it is determined that the third-party encounter should be initiated. As discussed above, medical intelligence process 56 may process 1004 the gathered encounter information (e.g., gathered encounter information 624) via artificial intelligence to determine whether a third-party encounter should be initiated. Accordingly, if medical intelligence process 56 determines that the third-party encounter with third-party entity 668 (e.g., a dermatologist and/or an oncologist) should be initiated, medical intelligence process 56 may automatically initiate 1012 the third-party encounter with third-party entity 668 (e.g., a dermatologist and/or an oncologist). Various factors may influence the above-described process. For example, medical intelligence process 56 may take into consideration various elements, examples of which may include but are not limited to: the particular area of specialization of the third-party encounter; whether the patient (e.g., user 538) is known by a particular third-party provider; if a particular third-party provider is in-network (for insurance purposes); and the general costs associated with a particular third-party provider.

When automatically initiating 1012 the third-party encounter if it is determined that the third-party encounter should be initiated, medical intelligence process 56 may determine 1014 whether third-party entity 668 (e.g., a dermatologist and/or an oncologist) is available to timely participate in the third-party encounter. Accordingly, medical intelligence process 56 may determine 1014 whether third-party entity 668 (e.g., a dermatologist and/or an oncologist) is available to join the medical encounter (e.g., the telehealth medical encounter) immediately (or within a reasonable amount of time).

Concept 7

As will be discussed below in greater detail, medical intelligence process 56 may be configured to provide supplement information for review by a medical professional (e.g., user 226 or user 542) during in-person medical encounters (e.g., via ambient cooperative intelligence process 10 and ACI system 54) and/or telehealth medical encounters (e.g., via telehealth process 510 and telehealth system 512). While the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Figure 17:
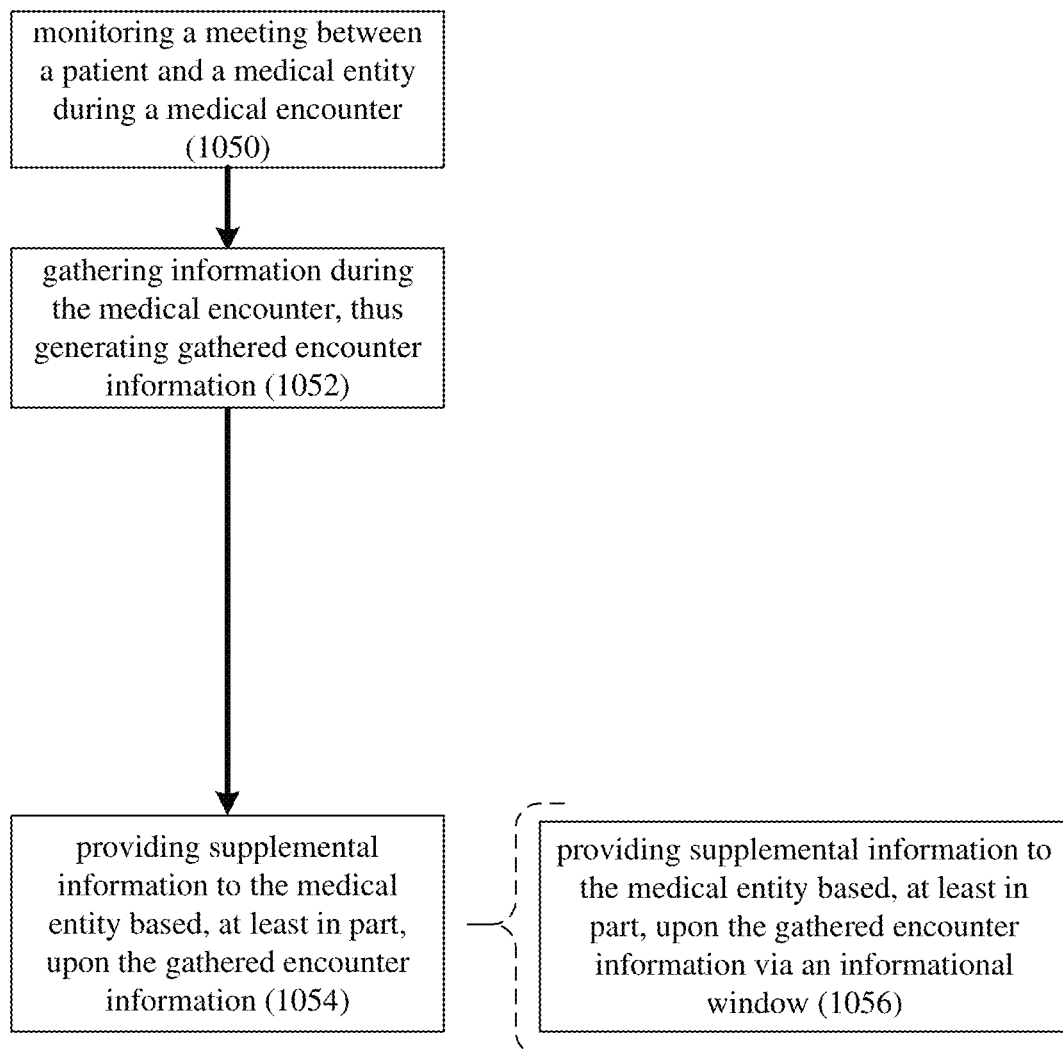
FIG. 17 is a flow chart of another implementation of the medical intelligence process of FIGS. 1 & 8.

Referring also to FIG. 17, medical intelligence process 56 may monitor 1050 a meeting between a patient (e.g., user 538) and a medical entity (e.g., user 542 and/or medical virtual assistant 630) during a medical encounter (e.g., a telehealth medical encounter).

Medical intelligence process 56 may gather 1052 information during the medical encounter (e.g., a telehealth medical encounter), thus generating gathered encounter information (e.g., gathered encounter information 624). Medical intelligence process 56 may provide 1054 supplemental information (e.g., supplemental information 638) to the medical entity (e.g., user 542) based, at least in part, upon the gathered encounter information (e.g., gathered encounter information 624).

As discussed above, supplemental information (e.g., supplemental information 638) may include one of more of: patient status information; EHR-provided information; patient-provided information; patient allergy information; patient medication information; medication interaction information; and AI-generated information.

Patient Status Information: The supplemental information (e.g., supplemental information 638) provided within the informational window (e.g., informational window 634) may include patient status information, examples of which may include but are not limited to patient name, address, phone number, emergency contact information, date of birth, height, weight, vital signs, allergies, current medications, insurance information. This patient status information may include current patient status information (e.g., patient status information at the time of the telehealth medical encounter) and historic patient status information (e.g., patient status information at some point prior to the telehealth medical encounter).

EHR-Provided Information: The supplemental information (e.g., supplemental information 638) provided within the informational window (e.g., informational window 634) may include EHR-provided information, examples of which may include but are not limited to any information that may be included within the electronic health record (EHR) of a patient (e.g., treatment history, illness history, etc.).

Patient-Provided Information: The supplemental information (e.g., supplemental information 638) provided within the informational window (e.g., informational window 634) may include patient-provided information, examples of which may include but are not limited to current aches, current pains, issues, and current concerns, as well as information included within the patient's health wallet (e.g., an electronic repository for the patient's health information that is controlled by the patient).

Patient Allergy Information: The supplemental information (e.g., supplemental information 638) provided within the informational window (e.g., informational window 634) may include patient allergy information (e.g., allergy information known by the patient that may not be included within the EHR of the patient).

Patient Medication Information: The supplemental information (e.g., supplemental information 638) provided within the informational window (e.g., informational window 634) may include patient medication information (e.g., medication information known by the patient that may not be included within the EHR of the patient).

Medication Interaction Information: The supplemental information (e.g., supplemental information 638) provided within the informational window (e.g., informational window 634) may include medication interaction information, examples of which may include but are not limited to known side effects/interactions of medication currently being taken by the patient and known side effects/interactions of medication being considered for the patient.

AI-Generated Information: The supplemental information (e.g., supplemental information 638) provided within the informational window (e.g., informational window 634) may include AI-generated information.

This AI-Generated Information may include one or more of: AI-generated best practices information; AI-generated medical encounter workflow information; AI-generated recommendations; AI-generated suggested inquiry information; and AI-generated observational information (each of which will be discussed below in greater detail).

AI-Generated Best Practices Information: The AI-Generated Best Practices Information may include information intended to define or provide guidance concerning one or more proposed best practices concerning e.g., the telehealth medical encounter.

AI-Generated Medical Encounter Workflow Information: The AI-Generated Medical Encounter Workflow Information may include information intended to define or provide guidance concerning one or more proposed workflows concerning e.g., the telehealth medical encounter.

AI-Generated Recommendations: The AI-Generated Recommendations may include information intended to define or provide guidance concerning one or more proposed recommendations concerning e.g., the telehealth medical encounter.

AI-Generated Suggested Inquiry Information: The AI-Generated Suggested Inquiry Information may include information intended to define or provide guidance concerning one or more proposed inquiries concerning e.g., the telehealth medical encounter.

AI-Generated Observational Information: The AI-Generated Observational Information may include information intended to provide observations concerning e.g., the telehealth medical encounter. This AI-Generated Observational Information may include one or more of: AI-generated audible observational information (e.g., observational information defined within audio-based content associated with e.g., the telehealth medical encounter), and AI-generated visual observational information (e.g., observational information defined within image-based content and/or video-based content associated with e.g., the telehealth medical encounter).

Generally speaking, medical intelligence process 56 may provide notifications and guidance to the medical entity (e.g., user 542) in a manner that gains the attention of the medical entity (e.g., user 542) without interfering with their ability to effectuate the medical encounter (e.g., an in-person medical encounter and/or a telehealth medical encounter). Medical intelligence process 56 may tag some or all of the supplemental information (e.g., supplemental information 638) provided to the medical entity (e.g., user 542) based upon severity. For example, low importance supplemental information may be provided to the medical entity (e.g., user 542) in a solid white font; medium importance supplemental information may be provided to the medical entity (e.g., user 542) in a solid red font; while high importance supplemental information may be provided to the medical entity (e.g., user 542) in a flashing red font. These visual notifications may automatically fade aware after a defined period of time; or may stay illuminated until the medical entity (e.g., user 542) "clicks" on the visual notification; or may stay illuminated until medical intelligence process 56 detects that the medical entity (e.g., user 542) addressed the visual notification during the medical encounter (e.g., an in-person medical encounter and/or a telehealth medical encounter). Additionally, these visual notifications may be supplemented with audible notifications (via a speaker assembly or an ear bud worn by user 542). As discussed above, medical intelligence process 56 may monitor 1050 the meeting between a patient (e.g., user 538) and a medical entity (e.g., user 542 and/or medical virtual assistant 630) during a medical encounter (e.g., an in-person medical encounter and/or a telehealth medical encounter). Accordingly, in the event that certain defined best practices appear to be missed by the medical entity (e.g., user 542), the supplemental information (e.g., supplemental information 638) provided by medical intelligence process 56 may remind the medical entity (e.g., user 542) to e.g., ask about current medications, discuss medication allergies, ask if there is anything else that needs to be discussed, etc.

When providing 1054 supplemental information (e.g., supplemental information 638) to the medical entity (e.g., user 542) based, at least in part, upon the gathered encounter information (e.g., gathered encounter information 624), medical intelligence process 56 may provide 1056 supplemental information (e.g., supplemental information 638) to the medical entity (e.g., user 542) based, at least in part, upon the gathered encounter information (e.g., gathered encounter information 624) via an informational window (e.g., informational window 634).

The informational window (e.g., informational window 634) may be a transparent overlay informational window. As discussed above, the informational window (e.g., informational window 634) may be configured to function in a similar fashion to a head-up display (i.e., positionable on top of other pieces of information without obscuring them), thus allowing the medical entity (e.g., user 542) to review the supplemental information (e.g., supplemental information 638) while fully participating in the telehealth medical encounter.

Medical intelligence process 56 may receive feedback concerning the supplemental information (e.g., supplemental information 638) from the medical entity (e.g., user 542). This feedback may be active, wherein medical intelligence process 56 may inquire as to whether the supplemental information was helpful. Additionally/alternatively, this feedback may be passive, wherein medical intelligence process 56 may gauge the quality of the supplemental information by monitoring whether the medical entity (e.g., user 542) follows the prompts of medical intelligence process 56.

Concept 8

As will be discussed below in greater detail, medical intelligence process 56 may be configured to provide medical encounter topical information for review by a medical professional (e.g., user 226 or user 542) during in-person medical encounters (e.g., via ambient cooperative intelligence process 10 and ACI system 54) and/or telehealth medical encounters (e.g., via telehealth process 510 and telehealth system 512). While the following illustrative example concerns medical intelligence process 56 being utilized during a telehealth medical encounter (e.g., via telehealth process 510 and telehealth system 512), it is understood that (as discussed above) medical intelligence process 56 may be utilized during in-person medical encounters and/or telehealth medical encounters.

Figure 18:
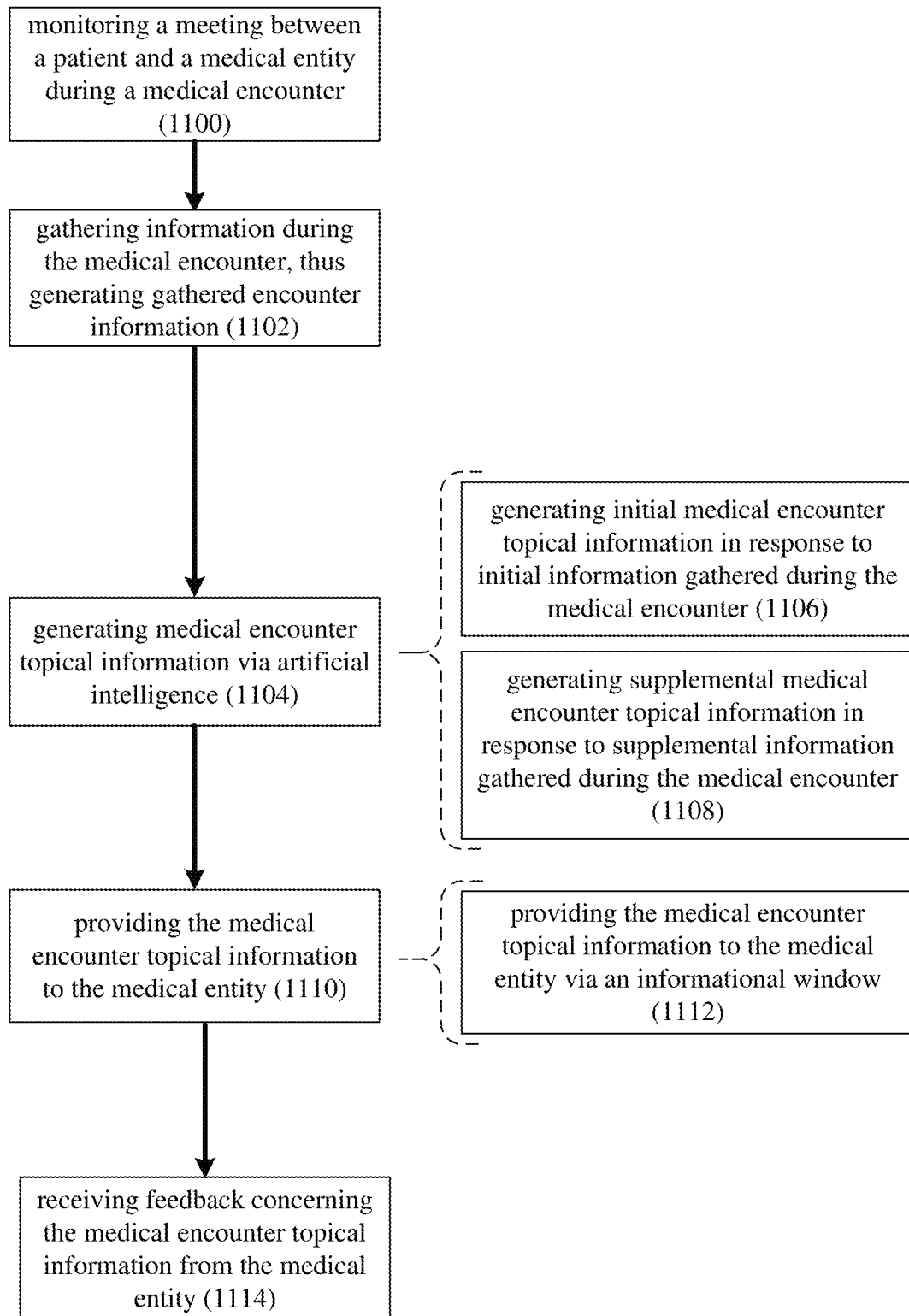
FIG. 18 is a flow chart of another implementation of the medical intelligence process of FIGS. 1 & 8.

Referring also to FIG. 18, medical intelligence process 56 may monitor 1100 a meeting between a patient (e.g., user 538) and a medical entity (e.g., user 542 and/or medical virtual assistant 630) during a medical encounter (e.g., a telehealth medical encounter).

Medical intelligence process 56 may gather 1102 information during the medical encounter (e.g., a telehealth medical encounter), thus generating gathered encounter information (e.g., gathered encounter information 624).

Medical intelligence process 56 may generate 1104 medical encounter topical information (e.g., medical encounter topical information 670) via artificial intelligence, wherein the medical encounter topical information (e.g., medical encounter topical information 670) may be based at least in part upon the gathered encounter information (e.g., gathered encounter information 624) and is configured to provide guidance to the medical entity (e.g., user 542) concerning one or more topics to be discussed during the medical encounter (e.g., an in-person medical encounter and/or a telehealth medical encounter). This medical encounter topical information (e.g., medical encounter topical information 670) may be based upon one or more best practices (e.g., best practices 644), wherein these one or more best practices (e.g., best practices 644) may be definable by one or more medical organizations/institutions (e.g., organizations/institutions 646).

When generating 1104 medical encounter topical information (e.g., medical encounter topical information 670) via artificial intelligence, medical intelligence process 56 may:
  generate 1106 initial medical encounter topical information (e.g., medical encounter topical information 670) in response to initial information gathered during the medical encounter (e.g., a telehealth medical encounter); and
  generate 1108 supplemental medical encounter topical information (e.g., medical encounter topical information 670) in response to supplemental information gathered during the medical encounter (e.g., a telehealth medical encounter).

Specifically, when medical intelligence process 56 has more knowledge as to what the medical encounter (e.g., a telehealth medical encounter) is about, the topics and progression thereof may be more defined. However, up until that point, the topics may be more fluid/wandering. For example, if the patient (e.g., user 538) is initially explaining to the medical entity (e.g., user 542) that they are having difficulty breathing, medical intelligence process 56 may initiate a first topic to investigate whether the patient (e.g., user 538) has COVID, notifying the medical entity (e.g., user 542) that "This Patient may have COVID" and prompting them to make inquiries about sense of taste and smell. In the event that it seems that the patient (e.g., user 538) does not have COVID, medical intelligence process 56 may initiate a second topic to investigate whether the patient (e.g., user 538) has pneumonia.

Generally speaking, medical intelligence process 56 may process data from previous visits with the medical entity (e.g., user 542), or in a particular hospital or in a group of hospitals to determine the manner in which a medical encounter (e.g., an in-person medical encounter and/or a telehealth medical encounter) should flow (e.g., the progression of the medical encounter, such as Topic A → Topic B → Topic C → Topic D → Topic E). The medical entity (e.g., user 542) may then be provided with prompts concerning proposed discussion topics. The sequencing of such topics may be definable by one or more medical organizations/institutions (e.g., organizations/institutions 646).

Medical intelligence process 56 may provide 1110 the medical encounter topical information (e.g., medical encounter topical information 670) to the medical entity (e.g., user 542). When providing 1110 the medical encounter topical information (e.g., medical encounter topical information 670) to the medical entity (e.g., user 542), medical intelligence process 56 may provide 1112 the medical encounter topical information (e.g., medical encounter topical information 670) to the medical entity (e.g., user 542) via an informational window (e.g., informational window 634).

The informational window (e.g., informational window 634) may be a transparent overlay informational window. As discussed above, the informational window (e.g., informational window 634) may be configured to function in a similar fashion to a head-up display (i.e., positionable on top of other pieces of information without obscuring them), thus allowing the medical entity (e.g., user 542) to review the medical encounter topical information (e.g., medical encounter topical information 670) while fully participating in the telehealth medical encounter Medical intelligence process 56 may receive 1114 feedback concerning the medical encounter topical information (e.g., medical encounter topical information 670) from the medical entity (e.g., user 542). This feedback may be active, wherein medical intelligence process 56 may inquire as to whether the medical encounter topical information was helpful. Additionally/alternatively, this feedback may be passive, wherein medical intelligence process 56 may gauge the quality of the medical encounter topical information by monitoring whether the medical entity (e.g., user 542) follows the prompts of medical intelligence process 56.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing system, comprising:
monitoring a meeting between a patient and a medical entity during a medical encounter;
gathering information during the medical encounter, thus generating gathered encounter information;
generating medical encounter topical information via artificial intelligence, wherein the medical encounter topical information is based at least in part upon the gathered encounter information and is configured to provide guidance to the medical entity concerning one or more topics to be discussed during the medical encounter;

providing the medical encounter topical information to the medical entity; and processing performance feedback concerning the medical encounter topical information provided by the medical entity, wherein the performance feedback includes one or more of an active component configured to prompt the medical entity to confirm whether or not the medical encounter topical information provided was helpful, and a passive component configured to monitor and compare actions taken by the medical entity with the guidance provided to the medical entity to determine a degree of compliance by the medical entity with the guidance provided.

2. The computer-implemented method of claim 1 wherein the medical entity includes one or more of:
   a medical professional; and
   a medical virtual assistant.

3. The computer-implemented method of claim 1 wherein the meeting includes one or more of:
   an intake portion;
   a consultation portion; and
   a follow-up portion.

4. The computer-implemented method of claim 1 wherein the medical encounter includes one or more of:
   an in-person medical encounter; and
   a telehealth medical encounter.

5. The computer-implemented method of claim 1 wherein providing the medical encounter topical information to the medical entity includes:
   providing the medical encounter topical information to the medical entity via an informational window.

6. The computer-implemented method of claim 5 wherein the informational window is a transparent overlay informational window.

7. The computer-implemented method of claim 1 wherein generating medical encounter topical information via artificial intelligence includes:
   generating initial medical encounter topical information in response to initial information gathered during the medical encounter; and
   generating supplemental medical encounter topical information in response to supplemental information gathered during the medical encounter.

8. The computer-implemented method of claim 1 wherein the medical encounter topical information is based upon one or more best practices.

9. The computer-implemented method of claim 8 wherein the one or more best practices are definable by one or more medical organizations/institutions.

10. A non-transitory computer readable medium having a plurality of instructions stored thereon which, when executed by a processor, cause the processor to perform operations comprising:
   monitoring a meeting between a patient and a medical entity during a medical encounter;
   gathering information during the medical encounter, thus generating gathered encounter information;
   generating medical encounter topical information via artificial intelligence, wherein the medical encounter topical information is based at least in part upon the gathered encounter information and is configured to provide guidance to the medical entity concerning one or more topics to be discussed during the medical encounter;
   providing the medical encounter topical information to the medical entity; and
   processing performance feedback concerning the medical encounter topical information provided by the medical entity, wherein the performance feedback includes one or more of an active component configured to prompt the medical entity to confirm whether or not the medical encounter topical information provided was helpful, and a passive component configured to monitor and compare actions taken by the medical entity with the guidance provided to the medical entity to determine a degree of compliance by the medical entity with the guidance provided.

11. The non-transitory computer readable medium of claim 10 wherein the medical entity includes one or more of:
   a medical professional; and
   a medical virtual assistant.

12. The non-transitory computer readable medium of claim 10 wherein the meeting includes one or more of:
   an intake portion;
   a consultation portion; and
   a follow-up portion.

13. The non-transitory computer readable medium of claim 10 wherein the medical encounter includes one or more of:
   an in-person medical encounter; and
   a telehealth medical encounter.

14. The non-transitory computer readable medium of claim 10 wherein providing the medical encounter topical information to the medical entity includes:
   providing the medical encounter topical information to the medical entity via an informational window.

15. The non-transitory computer readable medium of claim 14 wherein the informational window is a transparent overlay informational window.

16. The non-transitory computer readable medium of claim 10 wherein generating medical encounter topical information via artificial intelligence includes:
   generating initial medical encounter topical information in response to initial information gathered during the medical encounter; and
   generating supplemental medical encounter topical information in response to supplemental information gathered during the medical encounter.

17. The non-transitory computer readable medium of claim 10 wherein the medical encounter topical information is based upon one or more best practices.

18. The non-transitory computer readable medium of claim 17 wherein the one or more best practices are definable by one or more medical organizations/institutions.

19. A computing system including a processor and memory configured to perform operations comprising:
   monitoring a meeting between a patient and a medical entity during a medical encounter;
   gathering information during the medical encounter, thus generating gathered encounter information;
   generating medical encounter topical information via artificial intelligence, wherein the medical encounter topical information is based at least in part upon the gathered encounter information and is configured to provide guidance to the medical entity concerning one or more topics to be discussed during the medical encounter;
   providing the medical encounter topical information to the medical entity; and
   processing performance feedback concerning the medical encounter topical information provided by the medical entity, wherein the performance feedback includes one or more of an active component configured to prompt the medical entity to confirm whether or not the medical encounter topical information provided was helpful, and a passive component configured to monitor and compare actions taken by the medical entity with the guidance provided to the medical entity to determine a degree of compliance by the medical entity with the guidance provided.

20. The computing system of claim 19 wherein the medical entity includes one or more of:
   a medical professional; and
   a medical virtual assistant.

21. The computing system of claim 19 wherein the meeting includes one or more of:
   an intake portion;
   a consultation portion; and
   a follow-up portion.

22. The computing system of claim 19 wherein the medical encounter includes one or more of:
   an in-person medical encounter; and
   a telehealth medical encounter.

23. The computing system of claim 19 wherein providing the medical encounter topical information to the medical entity includes:
   providing the medical encounter topical information to the medical entity via an informational window.

24. The computing system of claim 23 wherein the informational window is a transparent overlay informational window.

25. The computing system of claim 19 wherein generating medical encounter topical information via artificial intelligence includes:
   generating initial medical encounter topical information in response to initial information gathered during the medical encounter; and
   generating supplemental medical encounter topical information in response to supplemental information gathered during the medical encounter.

26. The computing system of claim 19 wherein the medical encounter topical information is based upon one or more best practices.

27. The computing system of claim 26 wherein the one or more best practices are definable by one or more medical organizations/institutions.

* * * * *